United States Patent
Hodgkinson et al.

(10) Patent No.: US 11,512,290 B2
(45) Date of Patent: Nov. 29, 2022

(54) COMPOSITIONS AND METHODS FOR CELLULAR REPROGRAMMING

(71) Applicant: Duke University, Durham, NC (US)

(72) Inventors: Conrad Hodgkinson, Durham, NC (US); Victor Dzau, Durham, NC (US); Jaewoo Lee, Durham, NC (US); Bruce A. Sullenger, Durham, NC (US)

(73) Assignee: Duke University, Durham, NC (US)

( * ) Notice: Subject to any disclaimer, the term of this patent is extended or adjusted under 35 U.S.C. 154(b) by 0 days.

(21) Appl. No.: 16/982,964

(22) PCT Filed: Mar. 21, 2019

(86) PCT No.: PCT/US2019/023461
§ 371 (c)(1),
(2) Date: Sep. 21, 2020

(87) PCT Pub. No.: WO2019/183415
PCT Pub. Date: Sep. 26, 2019

(65) Prior Publication Data
US 2021/0017497 A1  Jan. 21, 2021

Related U.S. Application Data

(60) Provisional application No. 62/645,847, filed on Mar. 21, 2018, provisional application No. 62/782,480, filed on Dec. 20, 2018.

(51) Int. Cl.
| | | |
|---|---|---|
| *C07H 21/02* | (2006.01) | |
| *C12N 5/077* | (2010.01) | |
| *A61K 31/713* | (2006.01) | |
| *C12N 15/113* | (2010.01) | |

(52) U.S. Cl.
CPC .......... *C12N 5/0657* (2013.01); *A61K 31/713* (2013.01); *C12N 15/113* (2013.01); *C12N 2310/141* (2013.01); *C12N 2310/531* (2013.01); *C12N 2501/65* (2013.01); *C12N 2501/999* (2013.01)

(58) Field of Classification Search
CPC ......................... C12N 15/113; C12N 2310/141
See application file for complete search history.

(56) References Cited

U.S. PATENT DOCUMENTS

| | | |
|---|---|---|
| 9,987,309 B2 | 6/2018 | Dzau |
| 10,130,637 B2 | 11/2018 | Dzau |
| 10,695,378 B2 | 6/2020 | Dzau |
| 2014/0011281 A1 | 1/2014 | Dzau |
| 2016/0030332 A1 | 2/2016 | Lee |
| 2018/0042847 A1* | 2/2018 | Ross ..................... A61K 31/625 |
| 2018/0042969 A1 | 2/2018 | Wang |
| 2020/0345786 A1 | 11/2020 | Dzau |

FOREIGN PATENT DOCUMENTS

| | | |
|---|---|---|
| WO | 2013109763 A2 | 7/2013 |
| WO | 2018187328 A1 | 10/2018 |

OTHER PUBLICATIONS

Broughton et al. (Molecular Cell, 2016, 64, 320-333).*
Sirotkin et al. (Funct Integr Genomics, 2015, 15: 271-275).*
Kubler, K, et al. (2010). Targeted activation of RNA helicase retinoic acid-inducible gene-I induces proimmunogenic apoptosis of human ovarian cancer cells. Cancer Res 70: 5293-5304.
Kubler, K, et al. (2011). Immunogenic cell death of human ovarian cancer cells induced by cytosolic poly(I:C) leads to myeloid cell maturation and activates NK cells. Eur J Immunol 41: 3028-3039.
Lampkin, BC, et al. (1985). Phase II trial of a complex polyriboinosinic-polyribocytidylic acid with poly-L-lysine and carboxymethyl cellulose in the treatment of children with acute leukemia and neuroblastoma: a report from the Children's Cancer Study Group. Cancer Res 45: 5904-5909.
Lee, et al. (2013). Programming human dendritic cells with mRNA. Methods Mol Biol 969: 111-125.
Lee, et al. 2'Fluoro Modification Differentially Modulates the Ability of RNAs to Activate Pattern Recognition Receptors, Nucleic Acid Ther, 26 (2016) 173-182.
Lee, et al. Activated B cells modified by electroporation of multiple mRNAs encoding immune stimulatory molecules are comparable to mature dendritic cells in inducing in vitro antigen-specific T-cell responses, Immunology, 125 (2008) 229-240.
Lee, et al. Activation of innate immunity is required for efficient nuclear reprogramming. Cell. 2012;151:547-558.
Lee, et al. Peptide-enhanced mRNA transfection in cultured mouse cardiac fibroblasts and direct reprogramming towards cardiomyocyte-like cells, International journal of nanomedicine, 10 (2015) 1841-1854.
Li Y, et al. Tissue-engineered 3-dimensional (3D) microenvironment enhances the direct reprogramming of fibroblasts into cardiomyocytes by microRNAs. Sci Rep. 2016;6:38815.
Lin YT, et al. Toll-like receptors and human disease: lessons from single nucleotide polymorphisms. Curr Genomics. 2012;13:633-645.
Lion, E, et al (2011). Poly(I:C) enhances the susceptibility of leukemic cells to NK cell cytotoxicity and phagocytosis by DC. PLoS One 6: e20952.
Lluis, et al. E47 phosphorylation by p38 MAPK promotes MyoD/E47 association and muscle-specific gene transcription, The EMBO journal, 24 (2005) 974-984.
Mann DL. The emerging role of innate immunity in the heart and vascular system: for whom the cell tolls. Circ Res. 2011;108:1133-1145.
Matsushima-Miyagi, T, et al. (2012). TRAIL and Noxa are selectively upregulated in prostate cancer cells downstream of the RIG-I/MAVS signaling pathway by nonreplicating Sendai virus particles. Clin Cancer Res 18: 6271-6283.

(Continued)

*Primary Examiner* — Amy H Bowman
(74) *Attorney, Agent, or Firm* — Quarles & Brady LLP

(57) ABSTRACT

Disclosed herein are compositions and methods for cellular reprogramming. The compositions comprise one or more miRs and an activator of NFκB. Also provided are methods for enhancing or upregulating cardiomyocyte maturation in a cell or a subject and methods for inhibiting or downregulating cardiomyocyte maturation.

18 Claims, 16 Drawing Sheets

Specification includes a Sequence Listing.

(56) References Cited

OTHER PUBLICATIONS

Mumm, JB, et al. (2008). Cytokine-based transformation of immune surveillance into tumor-promoting inflammation. Oncogene 27: 5913-5919.
Nam YJ, et al. Induction of diverse cardiac cell types by reprogramming fibroblasts with cardiac transcription factors. Development. 2014;141:4267-4278.
Nam YJ, et al. Reprogramming of human fibroblasts toward a cardiac fate. Proc Natl Acad Sci U S A. 2013;110:5588-5593.
Obeid, M, et al. (2007). Calreticulin exposure dictates the immunogenicity of cancer cell death. Nat Med 13: 54-61.
O'Neill, et al. The family of five: TIR-domain-containing adaptors in Toll-like receptor signalling, Nature reviews. Immunology, 7 (2007) 353-364.
Palchetti, S, et al (2015). Transfected poly(I:C) activates different dsRNA receptors, leading to apoptosis or immunoadjuvant response in androgen-independent prostate cancer cells. J Biol Chem 290: 5470-5483.
Pandey, S, et al. (2015). Microbial sensing by Toll-like receptors and intracellular nucleic acid sensors. Cold Spring Harb Perspect Biol 7: a016246.
Peng, S, et al. (2009). Polyinosinic-polycytidylic acid liposome induces human hepatoma cells apoptosis which correlates to the up-regulation of RIG-I like receptors. Cancer Sci 100: 529-536.
Perdiguero, et al. Genetic analysis of p38 MAP kinases in myogenesis: fundamental role of p38alpha in abrogating myoblast proliferation, The EMBO journal, 26 (2007) 1245-1256.
Pichlmair, A, et al. (2011). IFIT1 is an antiviral protein that recognizes 5'-triphosphate RNA. Nat Immunol 12: 624-630.
Qian L, et al. In vivo reprogramming of murine cardiac fibroblasts into induced cardiomyocytes. Nature. 2012;485:593-598.
Robinson, N, et al. (2012). Type I interferon induces necroptosis in macrophages during infection with *Salmonella enterica* serovar Typhimurium. Nat Immunol 13: 954-962.
Sabbah, A, et al. (2009). Activation of innate immune antiviral responses by Nod2. Nat Immunol 10: 1073-1080.
Salaun, B, et al (2006). TLR3 can directly trigger apoptosis in human cancer cells. J Immunol 176: 4894-4901.
Sayed N, et al. Transdifferentiation of human fibroblasts to endothelial cells: role of innate immunity. Circulation. 2015;131:300-309.
Schmidt, A, et al. (2009). 5'-triphosphate RNA requires base-paired structures to activate antiviral signaling via RIG-I. Proc Natl Acad Sci U S A 106: 12067-12072.
Simeonov, et al. Direct reprogramming of human fibroblasts to hepatocyte-like cells by synthetic modified mRNAs, PLoS One, 9 (2014) e100134.
Simone, et al. p38 pathway targets SWI-SNF chromatin-remodeling complex to muscle-specific loci, Nature genetics, 36 (2004) 738-743.
Sioud, Induction of inflammatory cytokines and interferon responses by double-stranded and single-stranded siRNAs is sequence-dependent and requires endosomal localization, J Mol Biol, 348 (2005) 1079-1090.
Song K, et al. Heart repair by reprogramming non-myocytes with cardiac transcription factors. Nature. 2012;485:599-604.
Song, W, et al. (2015). Structural basis for specific recognition of single-stranded RNA by Toll-like receptor 13. Nat Struct Mol Biol 22: 782-787.
Strober, W, et al. (2011). NOD2, an intracellular innate immune sensor involved in host defense and Crohn's disease. Mucosal Immunol 4:484-495.
Thier, et al. Direct conversion of fibroblasts into stably expandable neural stem cells, Cell Stem Cell, 10 (2012) 473-479.
Trinchieri, Type I interferon: friend or foe?, The Journal of experimental medicine, 207 (2010) 2053-2063.
Twyman-Saint Victor, C, et al. (2015). Radiation and dual checkpoint blockade activate non-redundant immune mechanisms in cancer. Nature 520: 373-377.
Uzri, D, et al. (2009). Nucleotide sequences and modifications that determine RIG-I/RNA binding and signaling activities. J Virol 83: 4174-4184.
Vacchelli, E, et al. (2013). Trial Watch: Toll-like receptor agonists for cancer therapy. Oncoimmunology 2: e25238.
Vermes, I, et al. (1995). A novel assay for apoptosis. Flow cytometric detection of phosphatidylserine expression on early apoptotic cells using fluorescein labelled Annexin V. Journal of immunological methods 184: 39-51.
Wang X, et al. Selenium Augments microRNA Directed Reprogramming of Fibroblasts to Cardiomyocytes via Nanog. Sci Rep. 2016;6:23017.
Warren, et al. Highly efficient reprogramming to pluripotency and directed differentiation of human cells with synthetic modified mRNA, Cell Stem Cell, 7 618-630. 2010.
Yamakawa H, et al. Strategies for heart regeneration: approaches ranging from induced pluripotent stem cells to direct cardiac reprogramming. Int Heart J. 2015;56:1-5.
Yang, H, et al. (2013). The many faces of HMGB1: molecular structure-functional activity in inflammation, apoptosis, and chemotaxis. J Leukoc Biol 93: 865-873.
Yu, X, et al. (2016). Activation of the MDA5-IPS1 viral sensing pathway induces cancer cell death and type I interferon-dependent antitumor immunity. Cancer Res.
Zetser, et al. p38 mitogen-activated protein kinase pathway promotes skeletal muscle differentiation. Participation of the Mef2c transcription factor, The Journal of biological chemistry, 274 (1999) 5193-5200.
Zhao, et al. From fibroblasts to iPS cells: induced pluripotency by defined factors, Journal of cellular biochemistry, 105 (2008) 949-955.
Zhou, et al. Electroporation-mediated transfer of plasmids to the lung results in reduced TLR9 signaling and inflammation, Gene therapy, 14 (2007) 775-780.
Alonso, DF, et al (2011) Metastasis: recent discoveries and novel perioperative treatment strategies with particular interest in the hemostatic compound desmopressin. Curr Pharm Biotechnol 12: 1974-1980.
Andries, et al. Innate immune response and programmed cell death following carrier-mediated delivery of unmodified mRNA to respiratory cells, Journal of controlled release : official journal of the Controlled Release Society, 167 (2013) 157-166.
Angel, et al. Innate immune suppression enables frequent transfection with RNA encoding reprogramming proteins, PLoS One, 5 e11756. 2010.
Bakkar, et al. IKK/NF-kappaB regulates skeletal myogenesis via a signaling switch to inhibit differentiation and promote mitochondrial biogenesis, The Journal of cell biology, 180 (2008) 787-802.
Bakkar, et al. NF-kappaB signaling: a tale of two pathways in skeletal myogenesis, Physiological reviews, 90 (2010) 495-511.
Besch, R, et al. (2009). Proapoptotic signaling induced by RIG-I and MDA-5 results in type I interferon-independent apoptosis in human melanoma cells. J Clin Invest 119:2399-2411.
Blander, JM (2014). A long-awaited merger of the pathways mediating host defence and programmed cell death. Nat Rev Immunol 14: 601-618.
Bruneau BG. Signaling and transcriptional networks in heart development and regeneration. Cold Spring Harb Perspect Biol. 2013;5:a008292.
Bruneau BG. Transcriptional regulation of vertebrate cardiac morphogenesis. Circ Res. 2002;90:509-519.
Buganim Y, et al. Mechanisms and models of somatic cell reprogramming. Nat Rev Genet. 2013;14:427-439.
Cantone, et al. Epigenetic programming and reprogramming during development, Nature structural & molecular biology, 20 (2013) 282-289.
Cavalieri D, et al. Plant microRNAs as novel immunomodulatory agents. Sci Rep. 2016;6:25761.
Chattopadhyay, S, et al. (2010). Viral apoptosis is induced by IRF-3-mediated activation of Bax. EMBO J 29: 1762-1773.

(56) References Cited

OTHER PUBLICATIONS

Chawla-Sarkar, M, et al. (2001). Preferential induction of apoptosis by interferon (IFN)-beta compared with IFN-alpha2: correlation with TRAIL/Apo2L induction in melanoma cell lines. Clin Cancer Res 7: 1821-1831.
Dal-Pra S, et al. Demethylation of H3K27 Is Essential for the Induction of Direct Cardiac Reprogramming by miR Combo. Circ Res. 2017.
David L, et al. Phases of reprogramming. Stem Cell Res. 2014;12:754-761.
Davis, et al. Expression of a single transfected cDNA converts fibroblasts to myoblasts, Cell, 51 (1987) 987-1000.
Dogusan, et al. Double-stranded RNA induces pancreatic beta-cell apoptosis by activation of the toll-like receptor 3 and interferon regulatory factor 3 pathways, Diabetes, 57 (2008) 1236-1245.
Drews, et al. The cytotoxic and immunogenic hurdles associated with non-viral mRNA-mediated reprogramming of human fibroblasts, Biomaterials, 33 (2012) 4059-4068.
Duewell, P, et al. (2014). RIG-I-like helicases induce immunogenic cell death of pancreatic cancer cells and sensitize tumors toward killing by CD8(+) T cells. Cell Death Differ 21: 1825-1837.
Duewell, P, et al. (2015). Targeted activation of melanoma differentiation-associated protein 5 (MDA5) for immunotherapy of pancreatic carcinoma. Oncoimmunology 4: e1029698.
Epelman S, et al. Role of innate and adaptive immune mechanisms in cardiac injury and repair. Nat Rev Immunol. 2015;15:117-129.
Fabbri M, et al. MicroRNAs bind to Toll-like receptors to induce prometastatic inflammatory response. Proc Natl Acad Sci U S A. 2012;109:E2110-2116.
Faksh A, et al. TLR3 activation increases chemokine expression in human fetal airway smooth muscle cells. Am J Physiol Lung Cell Mol Physiol. 2016;310:L202-211.
Fu JD, et al. Direct reprogramming of human fibroblasts toward a cardiomyocyte-like state. Stem Cell Reports. 2013;1:235-247.
Gando, S, et al. (2015). Local hemostasis, immunothrombosis, and systemic disseminated intravascular coagulation in trauma and traumatic shock. Crit Care 19: 72.
Glas, M, et al. (2013). Targeting the cytosolic innate immune receptors RIG-I and MDA5 effectively counteracts cancer cell heterogeneity in glioblastoma. Stem Cells 31: 1064-1074.
Gou, et al. Epigenetic modification of TLRs in leukocytes is associated with increased susceptibility to *Salmonella enteritidis* in chickens, PloS one, 7 (2012) e33627.
Green, DR, et al (2009). Immunogenic and tolerogenic cell death. Nat Rev Immunol 9: 353-363.
He, et al. Toll-like receptors activate programmed necrosis in macrophages through a receptor-interacting kinase-3-mediated pathway, Proceedings of the National Academy of Sciences of the United States of America, 108 (2011) 20054-20059.
He, WA, et al. (2014). Microvesicles containing miRNAs promote muscle cell death in cancer cachexia via TLR7. Proc Natl Acad Sci U S A 111: 4525-1529.
Heil, F, et al. (2004). Species-specific recognition of single-stranded RNA via toll-like receptor 7 and 8. Science 303: 1526-1529.
Hodgkinson CP, et al. Abi3bp is a multifunctional autocrine/paracrine factor that regulates mesenchymal stem cell biology. Stem Cells 2013;31:1669-1682.
Hodgkinson CP, et al. Advanced glycation end-product of low density lipoprotein activates the toll-like 4 receptor pathway implications for diabetic atherosclerosis. Arterioscler Thromb Vase Biol. 2008;28:2275-2281.
Hodgkinson CP, et al. Toll-like receptors, their ligands, and atherosclerosis. ScientificWorldJournal. 2011;11:437-153.
International Searching Authority. International Search Report and Written Opinion for application PCT/US2019/023461. dated Jul. 25, 2019. 16 pages.
Ishibashi, et al. Short RNA duplexes elicit RIG-I-mediated apoptosis in a cell type- and length-dependent manner, Science signaling, 4 (2011) ra74.
Jayawardena TM, et al. Direct reprogramming of cardiac fibroblasts to cardiomyocytes using microRNAs. Methods Miol Biol. 2014;1150:263-272.
Jayawardena TM, et al. MicroRNA induced cardiac reprogramming in vivo: evidence for mature cardiac myocytes and improved cardiac function. Circ Res. 2015;116:418-424.
Jayawardena TM, et al. MicroRNA-mediated in vitro and in vivo direct reprogramming of cardiac fibroblasts to cardiomyocytes. Circ Res. 2012;110:1465-1473.
Jensen, S, et al. (2012). Sensing of RNA viruses: a review of innate immune receptors involved in recognizing RNA virus invasion. J Virol 86: 2900-2910.
Kaczanowska, S, et al. (2013). TLR agonists: our best frenemy in cancer immunotherapy. J Leukoc Biol 93: 847-863.
Kariko, et al. Incorporation of pseudouridine into mRNA yields superior nonimmunogenic vector with increased translational capacity and biological stability, Mol Ther, 16 (2008) 1833-1840.
Kariko, et al. Suppression of RNA recognition by Toll-like receptors: the impact of nucleoside modification and the evolutionary origin of RNA, Immunity, 23 (2005) 165-175.
Kato, H, et al. (2008). Length-dependent recognition of double-stranded ribonucleic acids by retinoic acid-inducible gene-I and melanoma differentiation-associated gene 5. J Exp Med 205: 1601-1610.
Kawai, et al. TLR signaling, Seminars in immunology, 19 (2007) 24-32.
Kazama, H, et al. (2008). Induction of immunological tolerance by apoptotic cells requires caspase-dependent oxidation of high-mobility group box-1 protein. Immunity 29: 21-32.
Kleinman, ME, et al. (2008). Sequence- and target-independent angiogenesis suppression by siRNA via TLR3. Nature 452: 591-597.
Kohlway, A, et al. (2013). Defining the functional determinants for RNA surveillance by Rig-I. EMBO Rep 14: 772-779.
Kroemer, G, et al. (2013). Immunogenic cell death in cancer therapy. Annual review of immunology 31: 51-72.
Hodgkinson CP, et al. "Cardiomyocyte maturation requires TLR3 activated nuclear factor kappa B." Stem Cells 36.8(2018): 1198-1209.
Hodgkinson CP, et al. Abstract 11279. "Direct Cardiac Reprogramming in Human Cardiac Fibroblasts via Micrornas." Circulation 140.Suppl_1 (2019).

\* cited by examiner

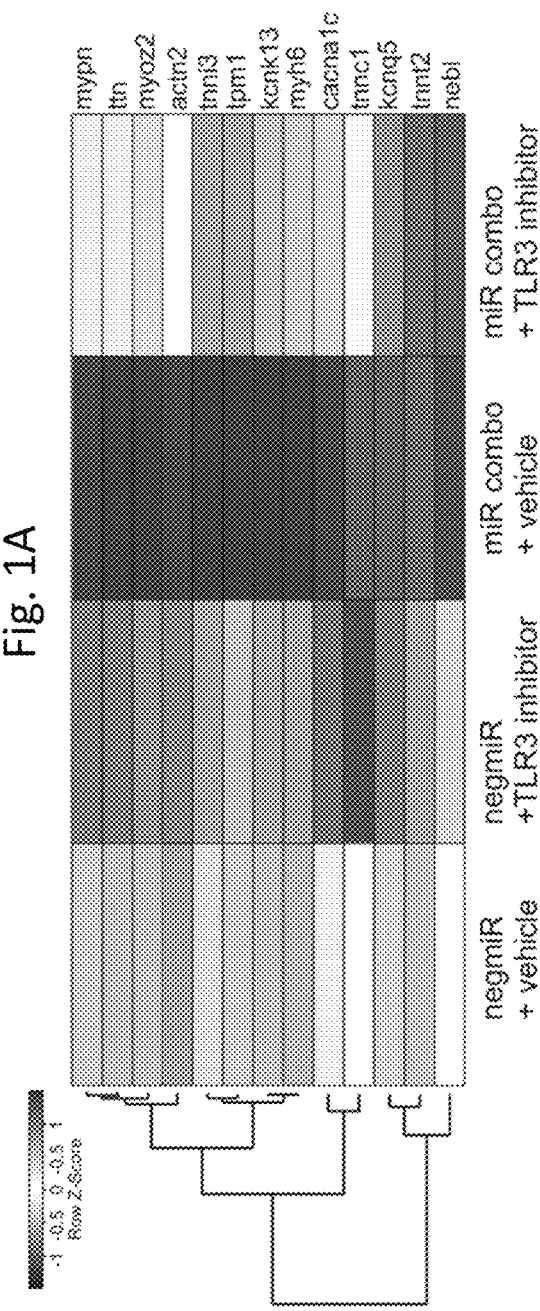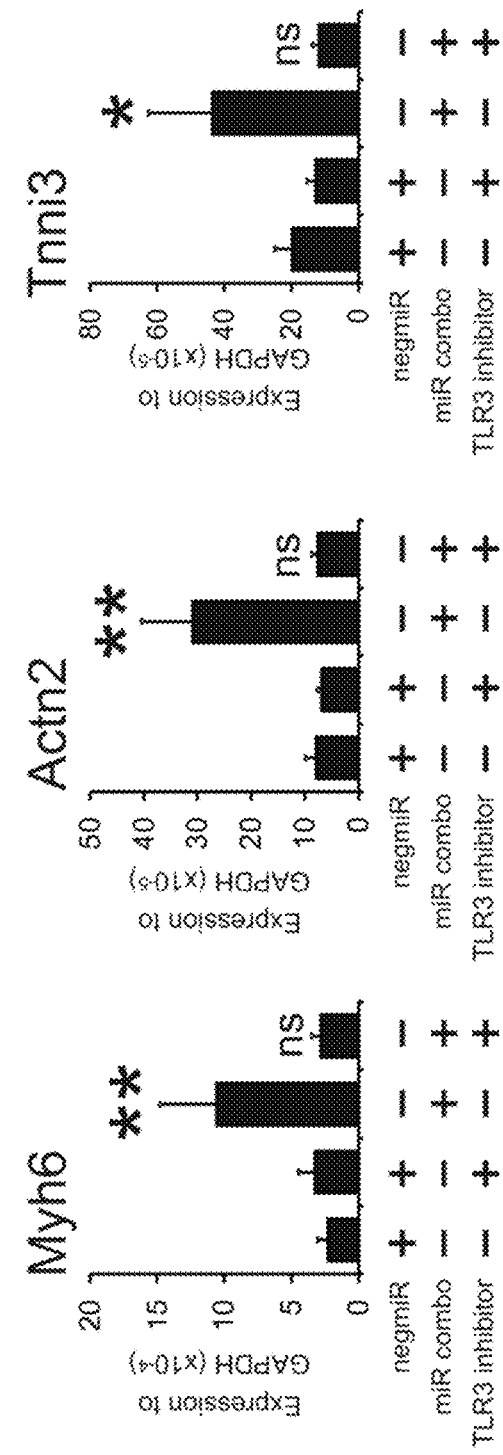

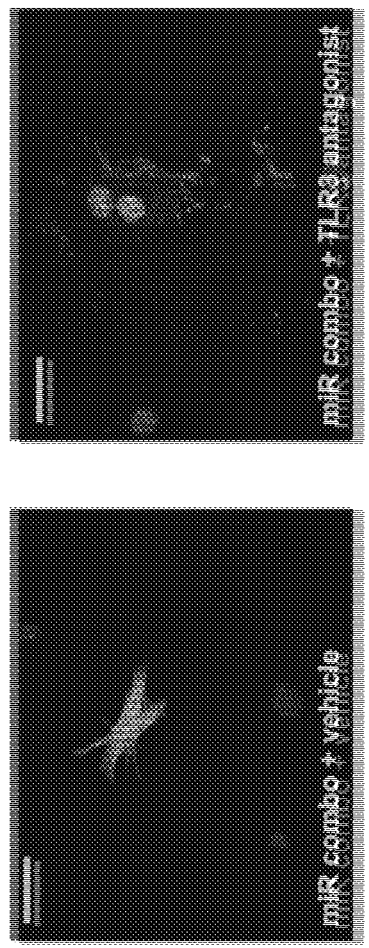
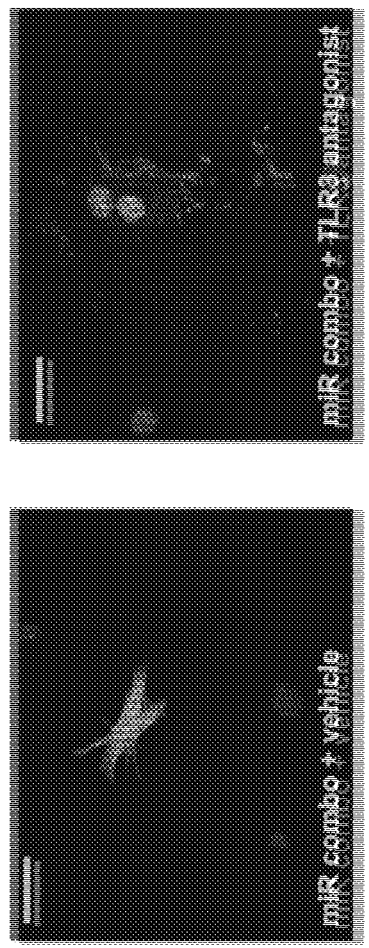
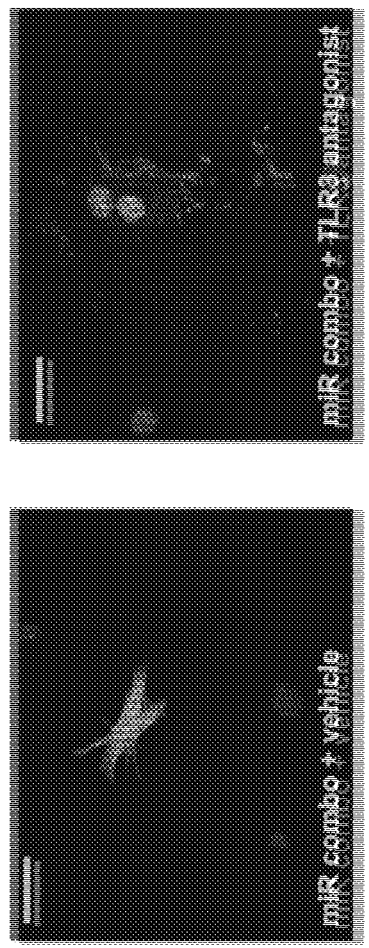
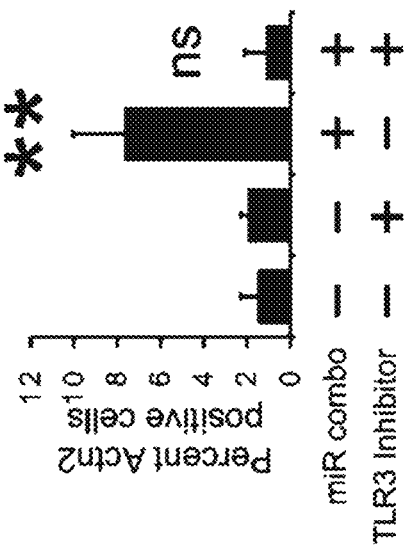
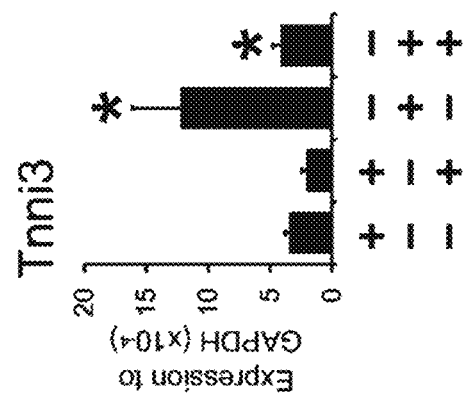
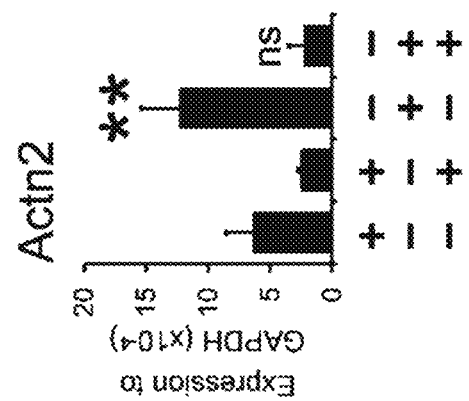
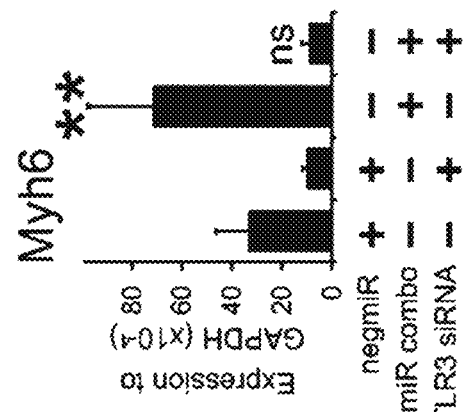
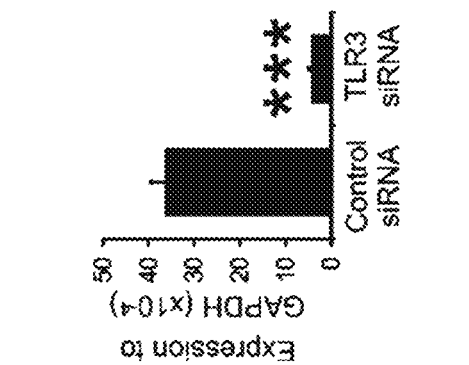

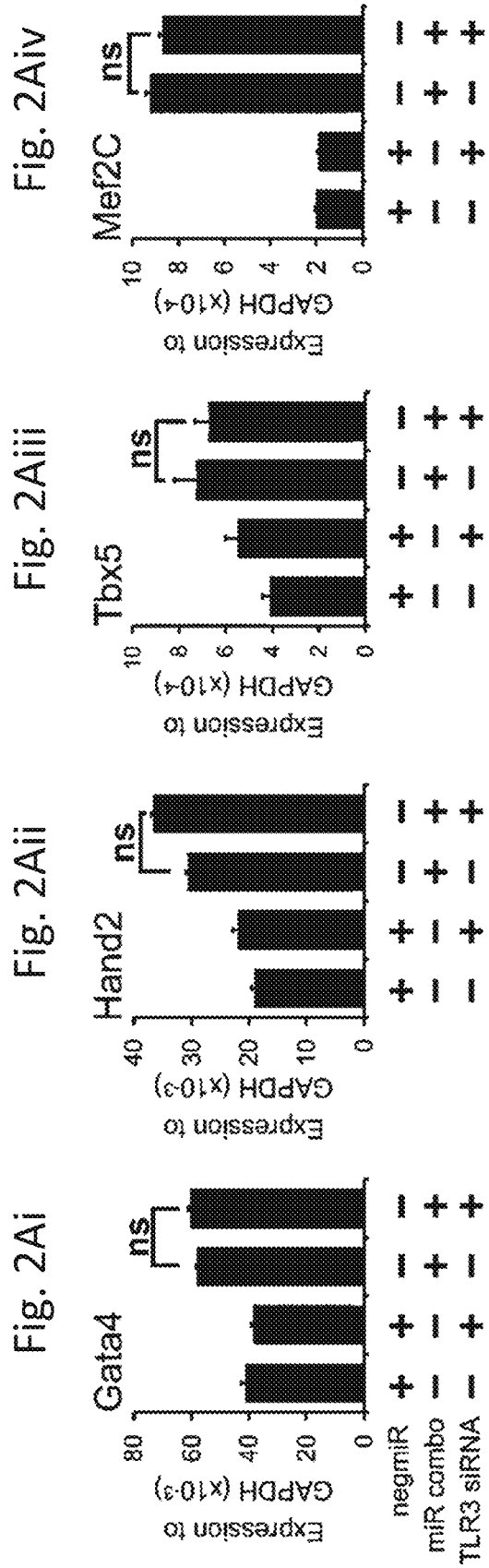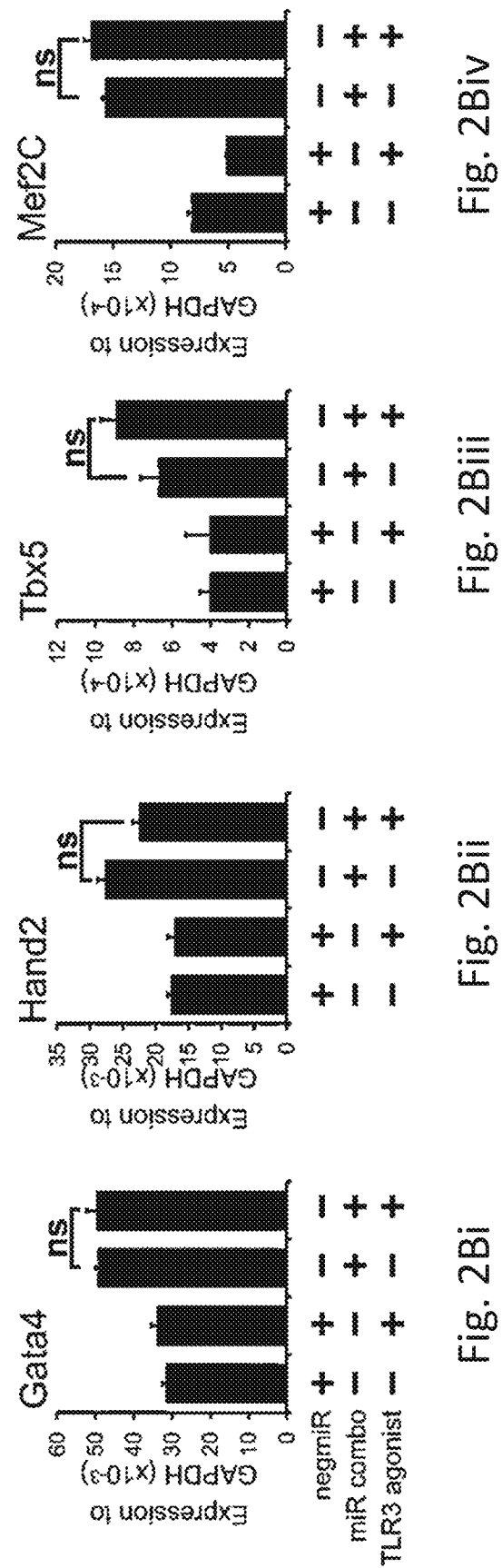

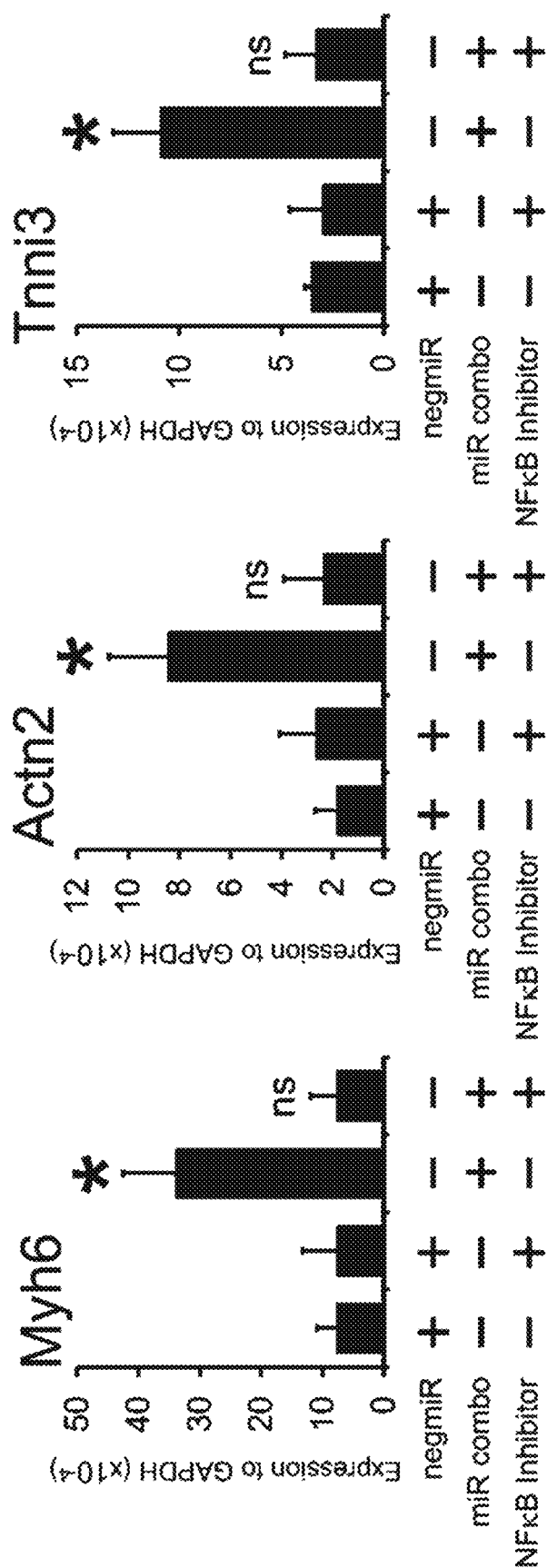
Fig. 3Ai  Fig. 3Aii  Fig. 3Aiii

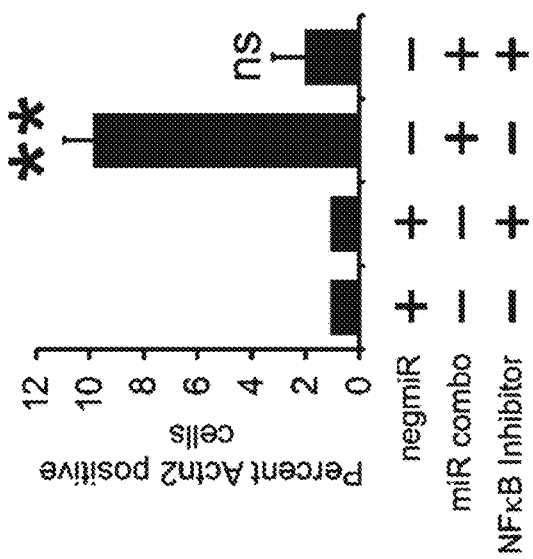
Fig. 3Bi  miR combo + vehicle
Fig. 3Bii  miR combo + NFκB Inhibitor
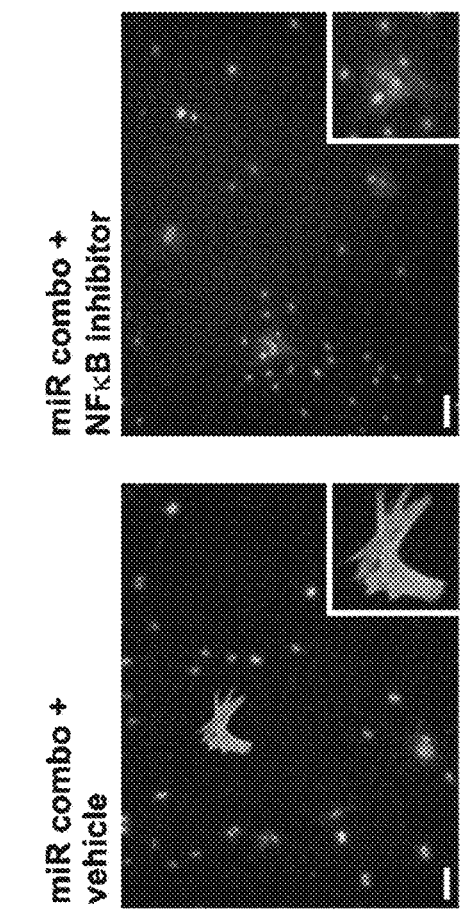
Fig. 3Biii
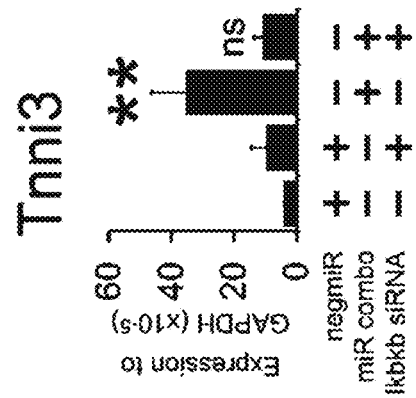
Fig. 3Di
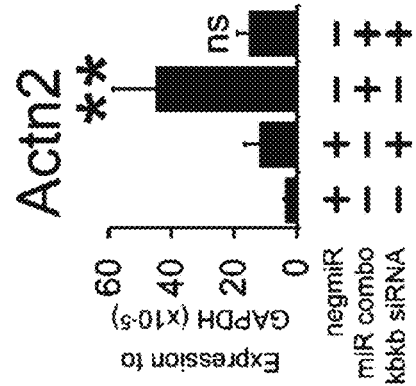
Fig. 3Dii
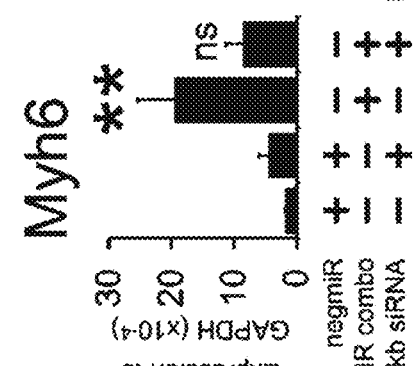
Fig. 3Diii
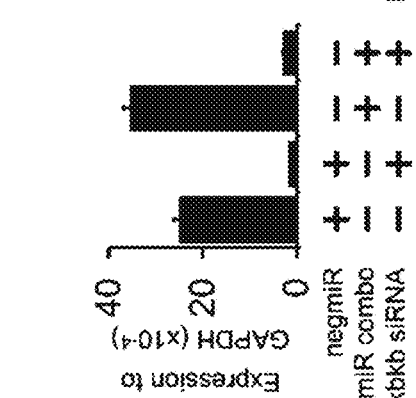
Fig. 3C

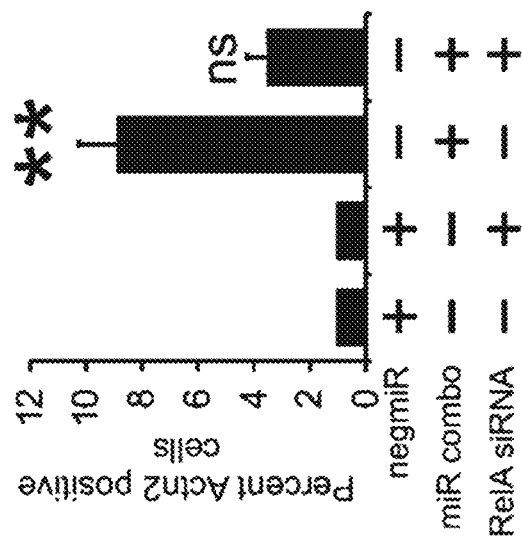
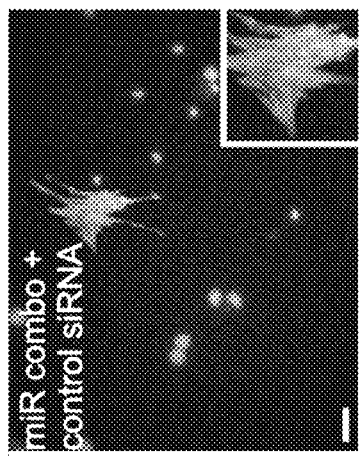
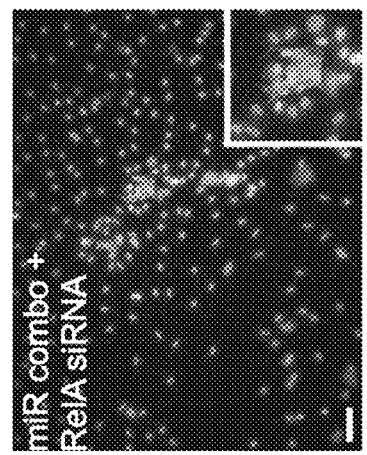
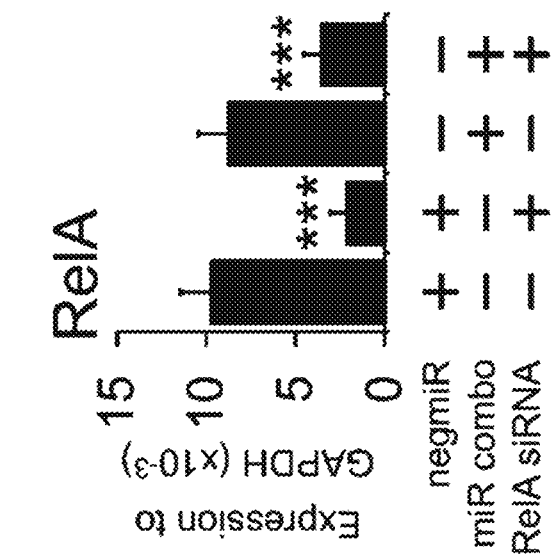

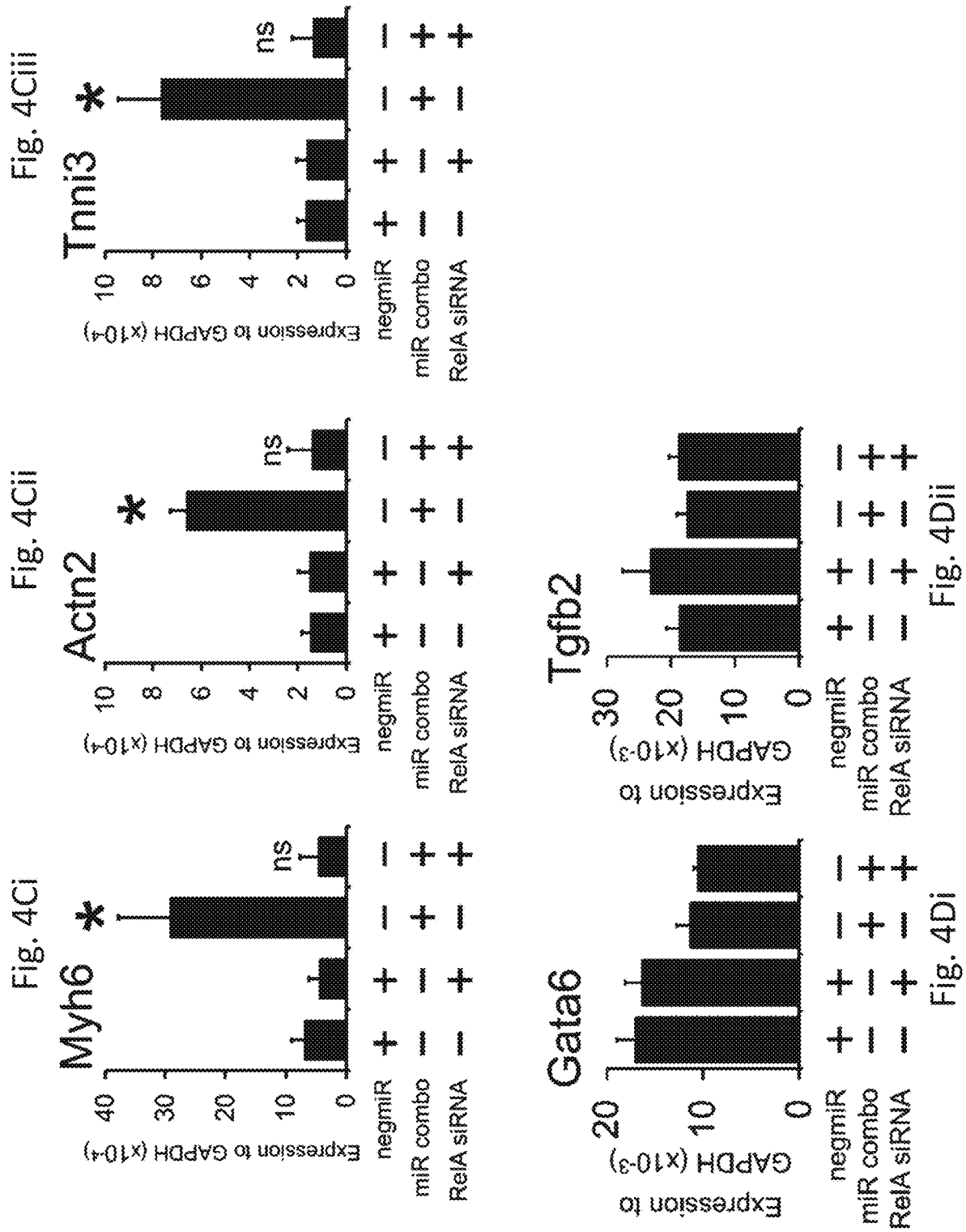

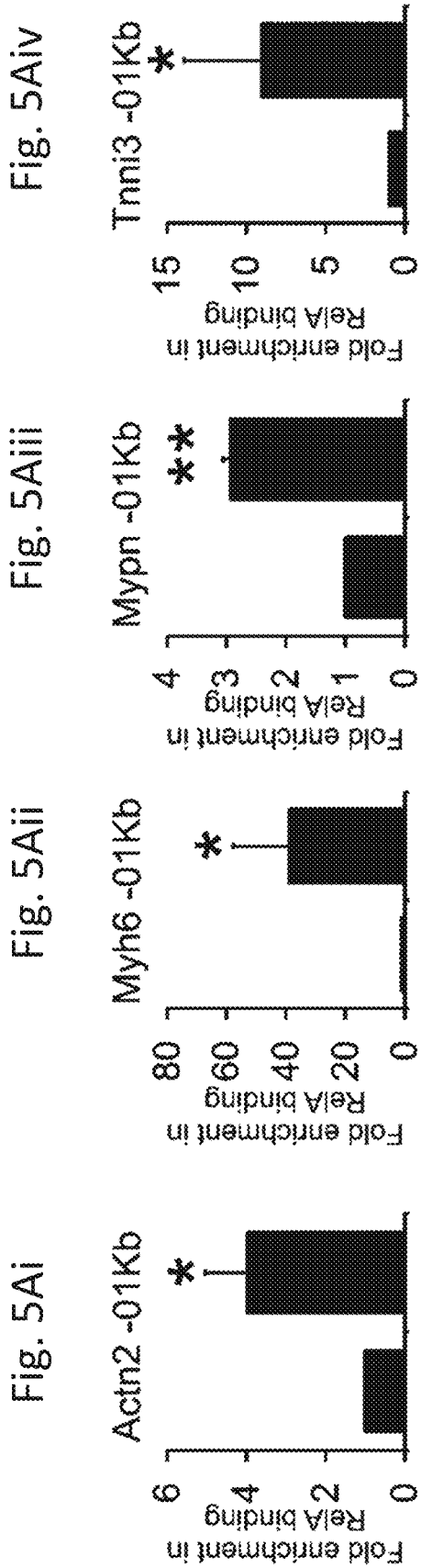
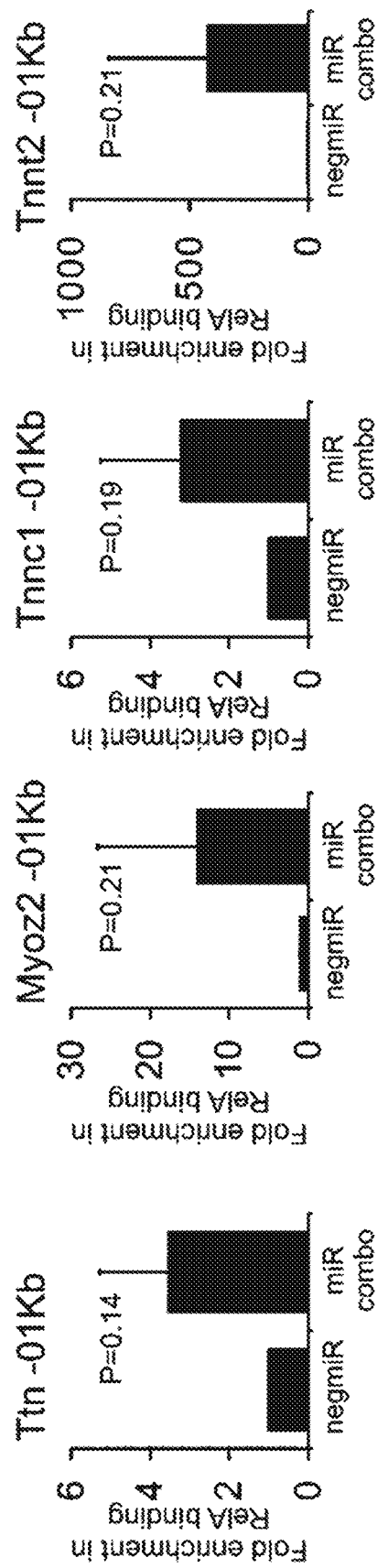

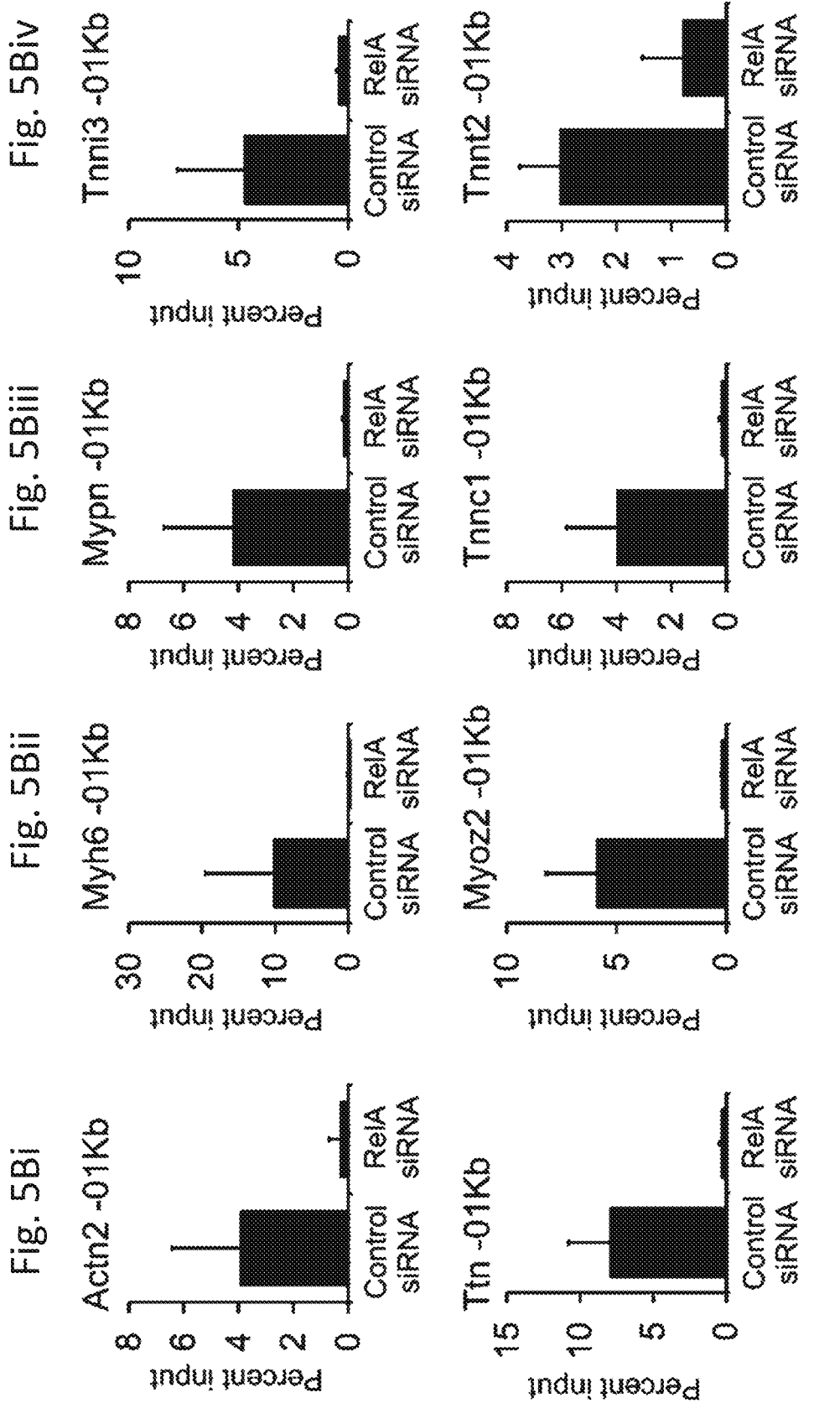

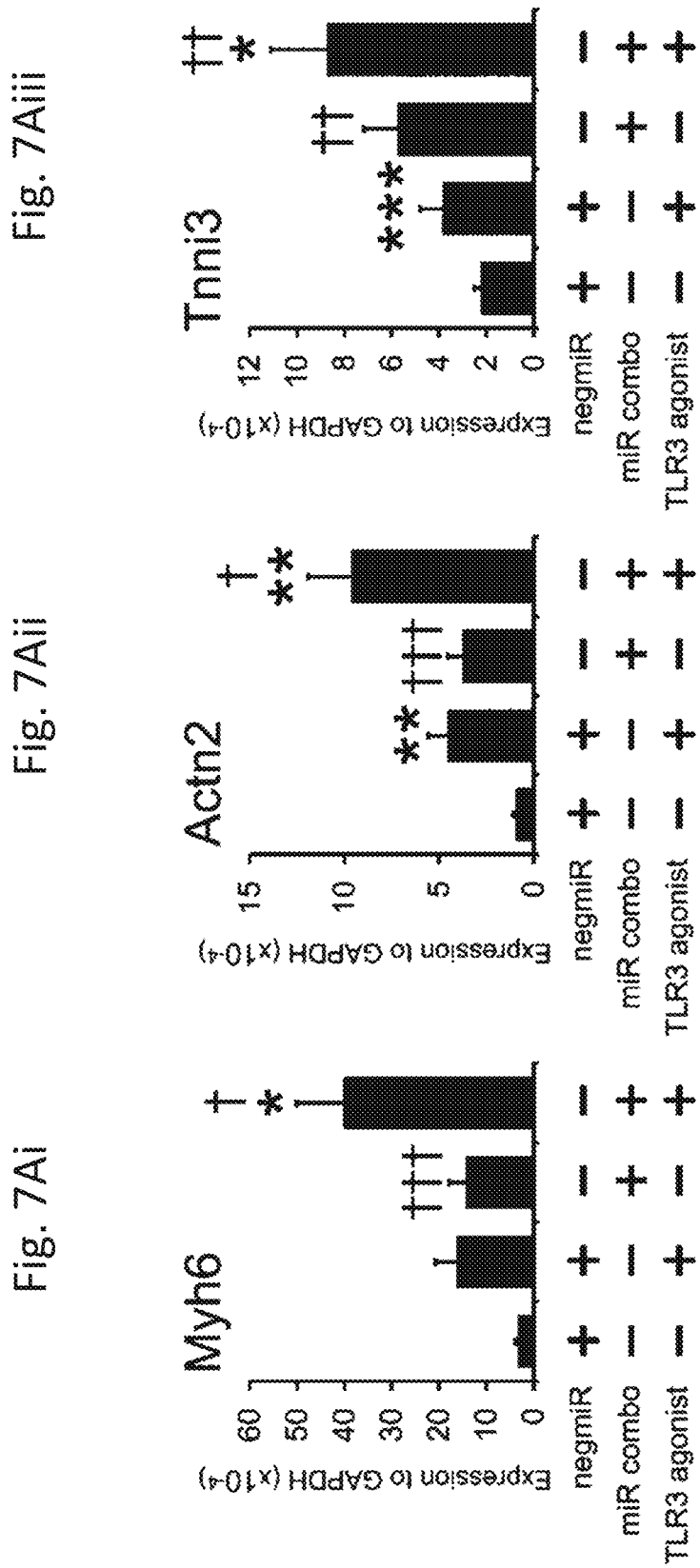

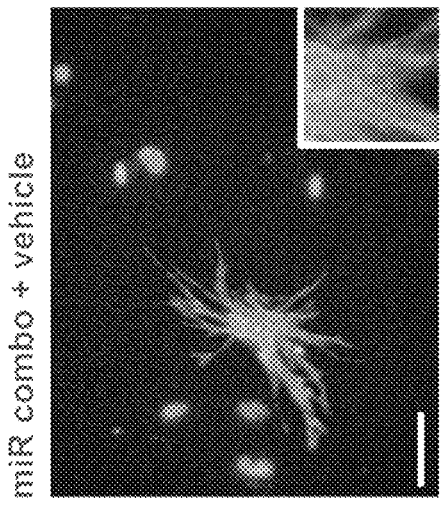
Fig. 7Bi
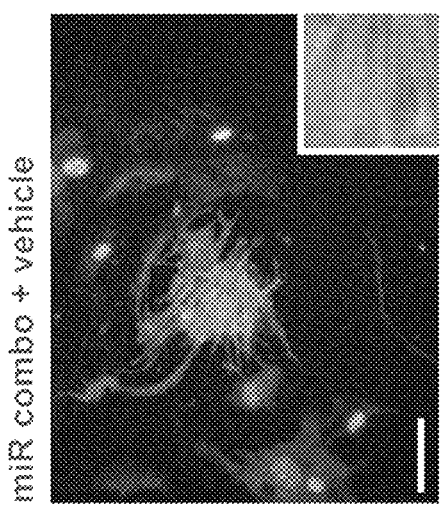
Fig. 7Bii
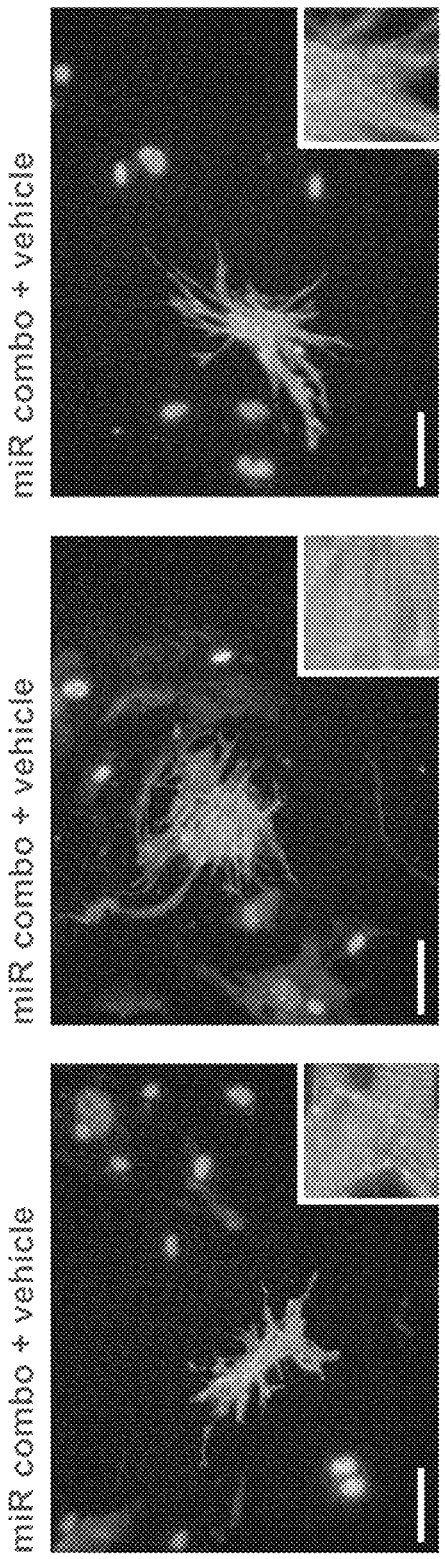
Fig. 7Biii
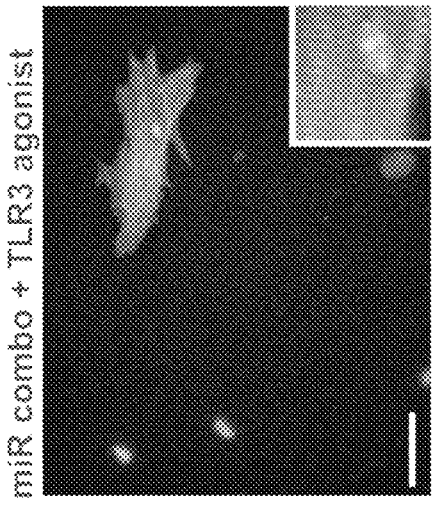
Fig. 7Biv
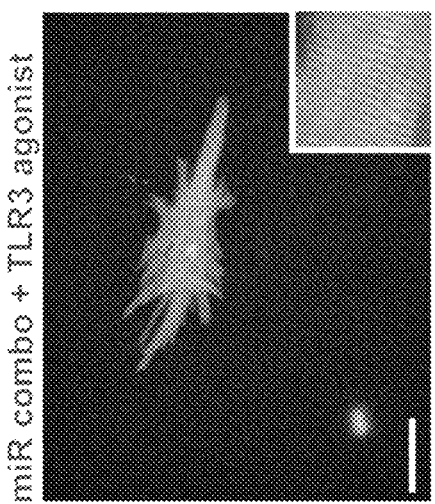
Fig. 7Bv
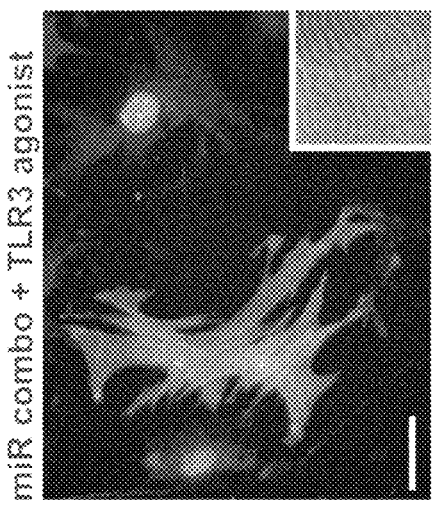
Fig. 7Bvi

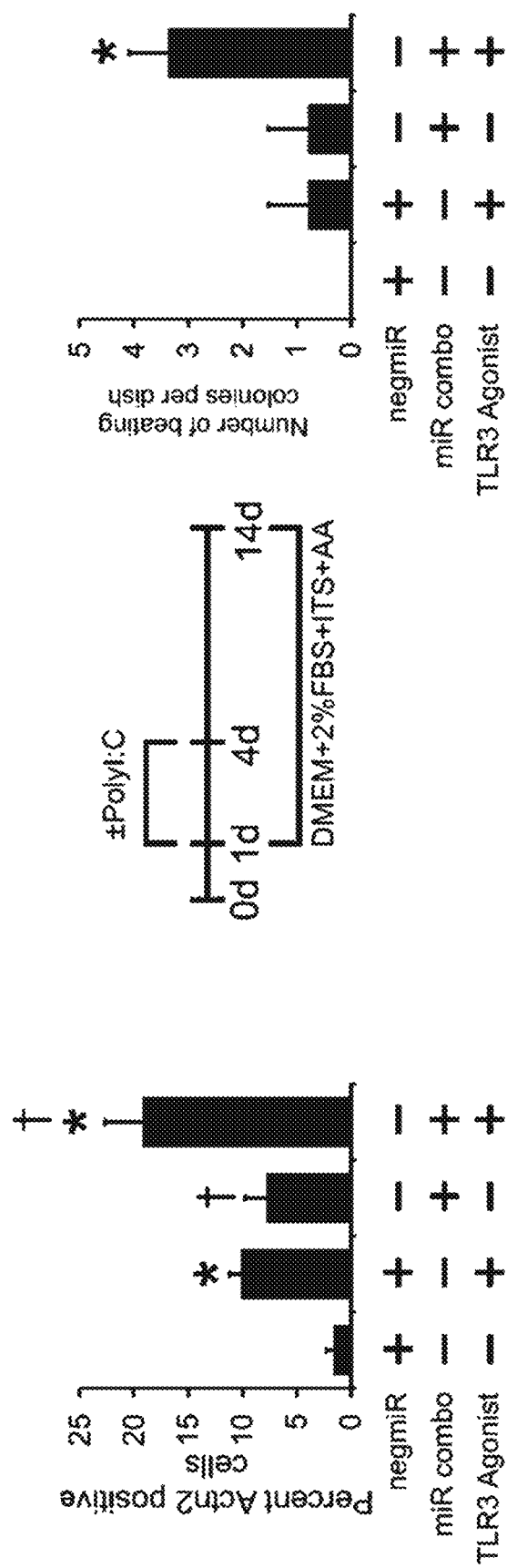

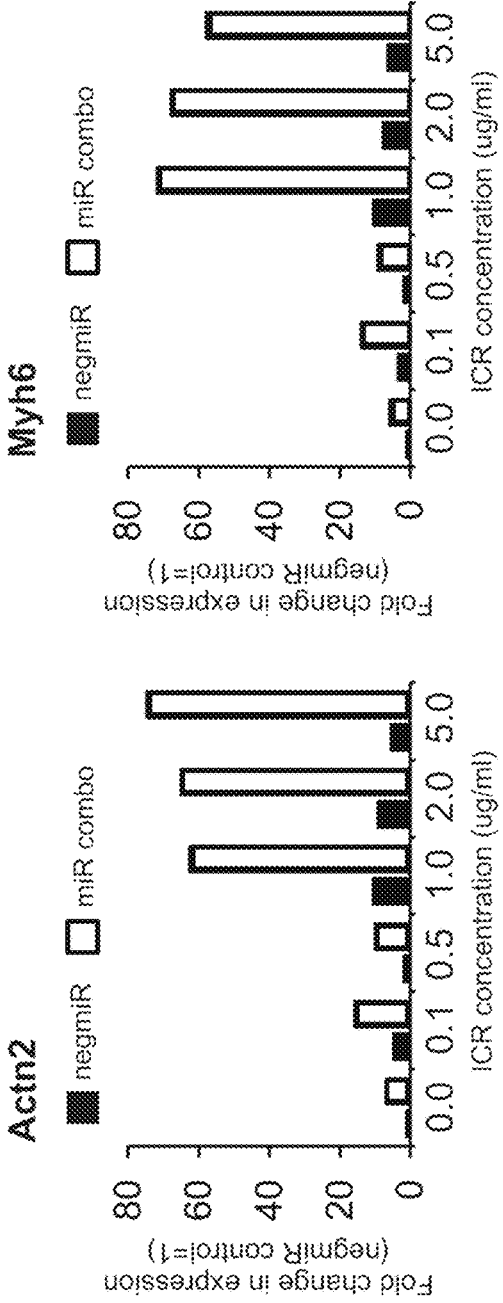
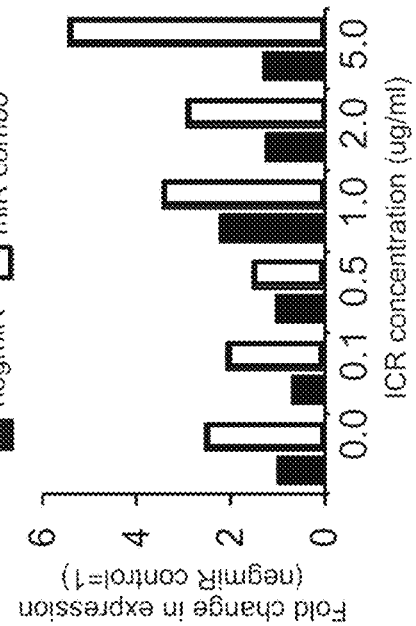
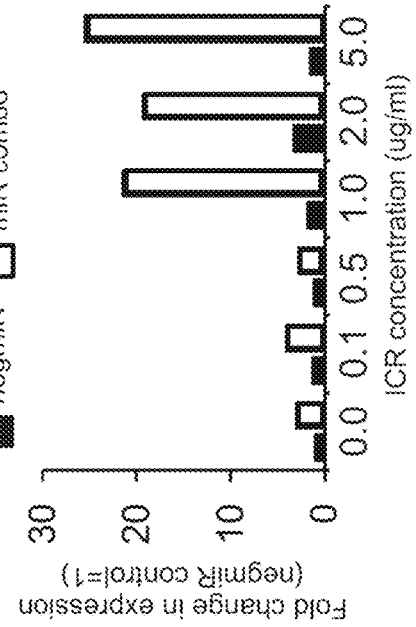
Fig. 8A, Fig. 8B, Fig. 8C, Fig. 8D

SEQUENCE LISTING

```
<160> NUMBER OF SEQ ID NOS: 45

<210> SEQ ID NO 1
<211> LENGTH: 77
<212> TYPE: RNA
<213> ORGANISM: Artificial Sequence
<220> FEATURE:
<223> OTHER INFORMATION: Mmu-miR-1 stem-loop

<400> SEQUENCE: 1
gcuugggaca cauacuucuu uauaugccca uaugaaccug cuaagcuaug gaauguaaag      60
aaguauguau uucaggc                                                    77

<210> SEQ ID NO 2
<211> LENGTH: 22
<212> TYPE: RNA
<213> ORGANISM: Artificial Sequence
<220> FEATURE:
<223> OTHER INFORMATION: Mmu-miR-1 mature

<400> SEQUENCE: 2
uggaauguaa agaaguaugu au                                              22

<210> SEQ ID NO 3
<211> LENGTH: 68
<212> TYPE: RNA
<213> ORGANISM: Artificial Sequence
<220> FEATURE:
<223> OTHER INFORMATION: Mmu-miR-133a stem-loop

<400> SEQUENCE: 3
gcuaaagcug guaaaaugga accaaaucgc cucuucaaug gauuuggucc ccuucaacca      60
gcuguagc                                                              68

<210> SEQ ID NO 4
<211> LENGTH: 22
<212> TYPE: RNA
<213> ORGANISM: Artificial Sequence
<220> FEATURE:
<223> OTHER INFORMATION: Mmu-miR-133a mature

<400> SEQUENCE: 4
uuuggucccc uucaaccagc ug                                              22

<210> SEQ ID NO 5
<211> LENGTH: 73
<212> TYPE: RNA
<213> ORGANISM: Artificial Sequence
<220> FEATURE:
<223> OTHER INFORMATION: Mmu-miR-206 stem-loop
```

<400> SEQUENCE: 5
ccaggccaca ugcuucuuua uauccucaua gauaucucag cacuauggaa uguaaggaag    60
ugugugguuu ugg    73

<210> SEQ ID NO 6
<211> LENGTH: 22
<212> TYPE: RNA
<213> ORGANISM: Artificial Sequence
<220> FEATURE:
<223> OTHER INFORMATION: Mmu-miR-206 mature

<400> SEQUENCE: 6
uggaauguaa ggaagugugu gg    22

<210> SEQ ID NO 7
<211> LENGTH: 83
<212> TYPE: RNA
<213> ORGANISM: Artificial Sequence
<220> FEATURE:
<223> OTHER INFORMATION: Mmu-miR-208a stem-loop

<400> SEQUENCE: 7
uuccuuugac gggugagcuu uuggcccggg uuauaccuga cacucacgua uaagacgagc    60
aaaaagcuug uuggucagag gag    83

<210> SEQ ID NO 8
<211> LENGTH: 22
<212> TYPE: RNA
<213> ORGANISM: Artificial Sequence
<220> FEATURE:
<223> OTHER INFORMATION: Mmu-miR-208a mature

<400> SEQUENCE: 8
auaagacgag caaaaagcuu gu    22

<210> SEQ ID NO 9
<211> LENGTH: 71
<212> TYPE: RNA
<213> ORGANISM: Artificial Sequence
<220> FEATURE:
<223> OTHER INFORMATION: Human miR-1-1 stem-loop

<400> SEQUENCE: 9
ugggaaacau acuucuuuau augcccauau ggaccugcua agcuauggaa uguaagaag     60 uauguaucuc a    71

<210> SEQ ID NO 10
<211> LENGTH: 85
<212> TYPE: RNA
<213> ORGANISM: Artificial Sequence
<220> FEATURE:
<223> OTHER INFORMATION: Human miR-1-2 stem-loop

<400> SEQUENCE: 10
accuacucag aguacauacu ucuuuaugua cccauaugaa cauacaaugc uauggaaugu    60
aaagaaguau guauuuuugg uaggc    85

<210> SEQ ID NO 11
<211> LENGTH: 22
<212> TYPE: RNA
<213> ORGANISM: Artificial Sequence
<220> FEATURE:
<223> OTHER INFORMATION: Mature sequence for both miR1 stem-loops

```
<400> SEQUENCE: 11
uggaauguaa agaaguaugu au                                              22

<210> SEQ ID NO 12
<211> LENGTH: 88
<212> TYPE: RNA
<213> ORGANISM: Artificial Sequence
<220> FEATURE:
<223> OTHER INFORMATION: Human miR-133a-1 stem-loop

<400> SEQUENCE: 12
acaaugcuuu gcuagagcug guaaaaugga accaaaucgc cucuucaaug gauuuggucc     60
ccuucaacca gcuguagcua ugcauuga                                        88

<210> SEQ ID NO 13
<211> LENGTH: 102
<212> TYPE: RNA
<213> ORGANISM: Artificial Sequence
<220> FEATURE:
<223> OTHER INFORMATION: Human miR-133a-2 stem-loop

<400> SEQUENCE: 13
gggagccaaa ugcuuugcua gagcugguaa aauggaacca aaucgacugu ccaauggauu     60 uggucccuu caaccagcug uagcugugca uugauggcgc cg                        102

<210> SEQ ID NO 14
<211> LENGTH: 22
<212> TYPE: RNA
<213> ORGANISM: Artificial Sequence
<220> FEATURE:
<223> OTHER INFORMATION: Mature sequence for both miR133a stem-loops

<400> SEQUENCE: 14
uuuggucccc uucaaccagc ug                                              22

<210> SEQ ID NO 15
<211> LENGTH: 86
<212> TYPE: RNA
<213> ORGANISM: Artificial Sequence
<220> FEATURE:
<223> OTHER INFORMATION: Human miR-206 stem-loop

<400> SEQUENCE: 15
ugcuucccga ggccacaugc uucuuuauau ccccauaugg auuacuuugc uauggaaugu     60
aaggaagugu gugguuucgg caagug                                          86

<210> SEQ ID NO 16
<211> LENGTH: 22
<212> TYPE: RNA
<213> ORGANISM: Artificial Sequence
<220> FEATURE:
<223> OTHER INFORMATION: Mature sequence for miR-206

<400> SEQUENCE: 16
uggaauguaa ggaagugugu gg                                              22

<210> SEQ ID NO 17
<211> LENGTH: 71
<212> TYPE: RNA
<213> ORGANISM: Artificial Sequence
<220> FEATURE:
<223> OTHER INFORMATION: Human miR-208a stem-loop
```

```
<400> SEQUENCE: 17
ugacgggcga gcuuuuggcc cggguuauac cugaugcuca cguauaagac gagcaaaaag    60
cuuguugguc a                                                        71

<210> SEQ ID NO 18
<211> LENGTH: 22
<212> TYPE: RNA
<213> ORGANISM: Artificial Sequence
<220> FEATURE:
<223> OTHER INFORMATION: Mature sequence for miR-208

<400> SEQUENCE: 18
auaagacgag caaaaagcuu gu                                            22

<210> SEQ ID NO 19
<211> LENGTH: 99
<212> TYPE: RNA
<213> ORGANISM: Artificial Sequence
<220> FEATURE:
<223> OTHER INFORMATION: Human miR-138-1 stem-loop

<400> SEQUENCE: 19
cccuggcaug guggugggg gcagcuggug uugugaauca ggccguugcc aaucagagaa    60
cggcuacuuc acaacaccag ggccacacca cacuacagg                          99

<210> SEQ ID NO 20
<211> LENGTH: 84
<212> TYPE: RNA
<213> ORGANISM: Artificial Sequence
<220> FEATURE:
<223> OTHER INFORMATION: Human miR-138-2 stem-loop

<400> SEQUENCE: 20
cguugcugca gcuggucuug ugaaucaggc cgacgagcag cgcauccucu uacccggcua    60
uuucacgaca ccaggguugc auca                                          84

<210> SEQ ID NO 21
<211> LENGTH: 23
<212> TYPE: RNA
<213> ORGANISM: Artificial Sequence
<220> FEATURE:
<223> OTHER INFORMATION: Mature sequence for both miR-138-1 and
      miR-138-2

<400> SEQUENCE: 21
agcugguguu gugaaucagg ccg                                           23

<210> SEQ ID NO 22
<211> LENGTH: 79
<212> TYPE: RNA
<213> ORGANISM: Artificial Sequence
<220> FEATURE:
<223> OTHER INFORMATION: Human miR-499-5p stem-loop

<400> SEQUENCE: 22 ggguggggcag cuguuaagac uugcagugau guuuagcucc ucugcaugug aacaucacag    60
caagucugug cugcugccu                                                79

<210> SEQ ID NO 23
<211> LENGTH: 21
<212> TYPE: RNA
<213> ORGANISM: Artificial Sequence
```

```
<220> FEATURE:
<223> OTHER INFORMATION: Mature Mmu-miR-499/Hsa-miR-499-5p; sequence is
      conserved

<400> SEQUENCE: 23
uuaagacuug cagugauguu u                                              21

<210> SEQ ID NO 24
<211> LENGTH: 30
<212> TYPE: RNA
<213> ORGANISM: Artificial Sequence
<220> FEATURE:
<223> OTHER INFORMATION: ICR1A

<400> SEQUENCE: 24
ggaugcggua ccugacagca uccuaaagug                                     30

<210> SEQ ID NO 25
<211> LENGTH: 41
<212> TYPE: RNA
<213> ORGANISM: Artificial Sequence
<220> FEATURE:
<223> OTHER INFORMATION: ICR1B

<400> SEQUENCE: 25
ggaugcggua ccugacagca uccuaaagug guggaaguga g                        41

<210> SEQ ID NO 26
<211> LENGTH: 56
<212> TYPE: RNA
<213> ORGANISM: Artificial Sequence
<220> FEATURE:
<223> OTHER INFORMATION: ICR1C

<400> SEQUENCE: 26
ggaugcggua ccugacagca uccuaaagug guggaaguga gugagugaaa uaaaaa        56

<210> SEQ ID NO 27
<211> LENGTH: 17
<212> TYPE: RNA
<213> ORGANISM: Artificial Sequence
<220> FEATURE:
<223> OTHER INFORMATION: ICR2-3

<400> SEQUENCE: 27
ggacguaccu gacgucc                                                   17

<210> SEQ ID NO 28
<211> LENGTH: 19
<212> TYPE: RNA
<213> ORGANISM: Artificial Sequence
<220> FEATURE:
<223> OTHER INFORMATION: ICR2-2

<400> SEQUENCE: 28
ggaucguacc ugacgaucc                                                 19

<210> SEQ ID NO 29
<211> LENGTH: 21
<212> TYPE: RNA
<213> ORGANISM: Artificial Sequence
<220> FEATURE:
<223> OTHER INFORMATION: ICR2-1

<400> SEQUENCE: 29
ggaucgguac cugacagauc c                                              21
```

```
<210> SEQ ID NO 30
<211> LENGTH: 23
<212> TYPE: RNA
<213> ORGANISM: Artificial Sequence
<220> FEATURE:
<223> OTHER INFORMATION: ICR2

<400> SEQUENCE: 30
ggaugcggua ccugacagca ucc                                              23

<210> SEQ ID NO 31
<211> LENGTH: 29
<212> TYPE: RNA
<213> ORGANISM: Artificial Sequence
<220> FEATURE:
<223> OTHER INFORMATION: ICR2A

<400> SEQUENCE: 31
ggacgaugcg guaccugaca gcaucgucc                                        29

<210> SEQ ID NO 32
<211> LENGTH: 51
<212> TYPE: RNA
<213> ORGANISM: Artificial Sequence
<220> FEATURE:
<223> OTHER INFORMATION: ICR2B

<400> SEQUENCE: 32
ggaugcggua ccugacagca uccaccuggg augcugucag guaccgcauc c               51

<210> SEQ ID NO 33
<211> LENGTH: 28
<212> TYPE: RNA
<213> ORGANISM: Artificial Sequence
<220> FEATURE:
<223> OTHER INFORMATION: ICR3

<400> SEQUENCE: 33
ggagcggaug cgguaccuga cagcaucc                                         28

<210> SEQ ID NO 34
<211> LENGTH: 35
<212> TYPE: RNA
<213> ORGANISM: Artificial Sequence
<220> FEATURE:
<223> OTHER INFORMATION: ICR3A

<400> SEQUENCE: 34
ggggaggaca gcggaugcgg uaccugacag caucc                                 35

<210> SEQ ID NO 35
<211> LENGTH: 42
<212> TYPE: RNA
<213> ORGANISM: Artificial Sequence
<220> FEATURE:
<223> OTHER INFORMATION: ICR3B

<400> SEQUENCE: 35
ggaaugaggg gaggacagcg gaugcgguac cugacagcau cc                         42

<210> SEQ ID NO 36
<211> LENGTH: 49
<212> TYPE: RNA
<213> ORGANISM: Artificial Sequence
<220> FEATURE:
<223> OTHER INFORMATION: ICR3C
```

<400> SEQUENCE: 36
ggguaaguga augaggggag dacagcggau gcgguaccug acagcaucc            49

<210> SEQ ID NO 37
<211> LENGTH: 55
<212> TYPE: RNA
<213> ORGANISM: Artificial Sequence
<220> FEATURE:
<223> OTHER INFORMATION: ICR4

<400> SEQUENCE: 37
ggaugcggua ccugacagca uccuaaacuc augguccaug uuuguccaug gacca      55

<210> SEQ ID NO 38
<211> LENGTH: 86
<212> TYPE: RNA
<213> ORGANISM: Artificial Sequence
<220> FEATURE:
<223> OTHER INFORMATION: ICR4A

<400> SEQUENCE: 38
ggaugcggua ccugacagca uccuaaacuc augguccaug uuuguccaug gaccaacuac    60
cgacauugua uguuugaua uaaugu                                          86

<210> SEQ ID NO 39
<211> LENGTH: 39
<212> TYPE: RNA
<213> ORGANISM: Artificial Sequence
<220> FEATURE:
<223> OTHER INFORMATION: ICR5X

<400> SEQUENCE: 39
ggaugcggua ccugacagca uccugaguuu aguuguugu                        39

<210> SEQ ID NO 40
<211> LENGTH: 39
<212> TYPE: RNA
<213> ORGANISM: Artificial Sequence
<220> FEATURE:
<223> OTHER INFORMATION: ICR5Y

<400> SEQUENCE: 40
ggaugcggua ccugacagca uccacaacaa cuaaacuca                        39

<210> SEQ ID NO 41
<211> LENGTH: 23
<212> TYPE: RNA
<213> ORGANISM: Artificial Sequence
<220> FEATURE:
<223> OTHER INFORMATION: ICR-L

<400> SEQUENCE: 41
gguuuuuuuu uuuuuuuuu uuu                                          23

<210> SEQ ID NO 42
<211> LENGTH: 85
<212> TYPE: RNA
<213> ORGANISM: Artificial Sequence
<220> FEATURE:
<223> OTHER INFORMATION: Human miR-126 stem-loop

<400> SEQUENCE: 42
cgcuggcgac gggacauuau acuuuuggu acgcgcugug acacuucaaa cucguaccgu     60
gaguaauaau gcgccgucca cggca                                          85

```
<210> SEQ ID NO 43
<211> LENGTH: 22
<212> TYPE: RNA
<213> ORGANISM: Artificial Sequence
<220> FEATURE:
<223> OTHER INFORMATION: Mature sequence for miR-126

<400> SEQUENCE: 43
ucguaccgug aguaauaaug cg                                               22

<210> SEQ ID NO 44
<211> LENGTH: 21
<212> TYPE: RNA
<213> ORGANISM: Artificial Sequence
<220> FEATURE:
<223> OTHER INFORMATION: miR-126-5p

<400> SEQUENCE: 44
cauuauuacu uuugguacgc g                                                21

<210> SEQ ID NO 45
<211> LENGTH: 25
<212> TYPE: RNA
<213> ORGANISM: Artificial Sequence
<220> FEATURE:
<223> OTHER INFORMATION: ICR1

<400> SEQUENCE: 45
ggaugcggua ccugacagca uccua                                            25
```

COMPOSITIONS AND METHODS FOR CELLULAR REPROGRAMMING

CROSS-REFERENCE TO RELATED APPLICATIONS

This patent application is a national stage filing under 35 U.S.C. § 371 of International Application No. PCT/US2019/023461, filed Mar. 21, 2019, which claims the benefit of priority of U.S. Provisional Patent Application No. 62/645,847, filed Mar. 21, 2018 and 62/782,480, filed Dec. 20, 2018, the contents of each are incorporated herein by reference in their entirety.

CROSS-REFERENCE TO RELATED APPLICATION

This patent application claims the benefit of priority of United States Provisional Patent Applications Nos. 62/645,847, filed Mar. 21, 2018, and 62/782,480, filed Dec. 20, 2018, the contents of each are incorporated herein by reference in their entirety.

BACKGROUND

Heart disease is the number one killer of men and women worldwide. Generally, heart tissue has a limited capacity for regeneration or self-renewal. After a patient recovers from a myocardial infarction, the organ bears a scar and heart function is diminished. The ability to regenerate damaged organs such as the heart remains elusive. As such, there is a pressing need in the art to develop new strategies for the regeneration of damaged organs.

BRIEF SUMMARY OF THE INVENTION

Disclosed herein are compositions and methods for cellular reprogramming. One aspect of the invention is a reprogramming composition comprising one or more miRs comprising a nucleotide sequence having at least 80% sequence identity to miR-1, miR-126, miR-133, miR-133a, mir-206, miR-208, miR-499, mir-499-5p, and combinations thereof; and an activator of NFκB.

Another aspect of the invention is a pharmaceutical composition including an effective amount of the composition of claim 1 and one or more pharmaceutically acceptable carriers, excipients, or diluents.

Another aspect of the invention is a method for enhancing or upregulating cardiomyocyte maturation in a cell comprising contacting the cell with an effective amount of any of the compositions described herein for a sufficient time such that the cell is reprogrammed into a cardiomyocyte.

Another aspect of the invention is a method of enhancing or upregulating cardiomyocyte maturation in a subject comprising administering (i) an effective amount of any of the compositions described or (ii) any of the pharmaceutical compositions comprising the effective amount of any of the compositions described and one or more pharmaceutically acceptable carriers, excipients, or diluents.

Another aspect of the invention is a method for inhibiting or downregulating cardiomyocyte maturation in a cell comprising contacting the cell with an effective amount of a composition comprising a TLR3 inhibitor, a NFκB inhibitor, a ikbkb inhibitor, or a combination thereof for a sufficient time such that cardiomyocyte maturation is inhibited or down-regulated in the cell.

BRIEF DESCRIPTION OF THE DRAWINGS

Non-limiting embodiments of the present invention will be described by way of example with reference to the accompanying figures, which are schematic and are not intended to be drawn to scale. In the figures, each identical or nearly identical component illustrated is typically represented by a single numeral. For purposes of clarity, not every component is labeled in every figure, nor is every component of each embodiment of the invention shown where illustration is not necessary to allow those of ordinary skill in the art to understand the invention.

FIGS. 1A-1Eiii show TLR3 inhibition inhibits maturation of reprogrammed fibroblasts into cardiomyocytes. Neonatal cardiac fibroblasts were transfected with negative control miR (negmiR) or miR combo. The day after transfection media was replaced and the cells incubated with either vehicle or the TLR3 pharmacological inhibitor CU-CPT-4a (10 µM) for a further 4 days. After incubation with the TLR3 pharmacological inhibitor, cells were cultured in normal growth media for a further 6 days. Quantitative PCR was used to analyze mRNA levels of 13 components of the cardiomyocyte sarcomere.

FIG. 1A shows a heat-map overview of the qPCR analysis. Expression values were normalized to the average expression of the negmiR vehicle samples and then averaged (N=3 technical replicates (fibroblasts were derived from single litter and seeded into 3 individual wells). Averages for each gene were then converted to Z-scores. Centroid linkage and Euclidean methods were employed for clustering and distance measurements respectively.

FIGS. 1Bi-1Ciii show neonatal cardiac fibroblasts were transfected with negative control miR (negmiR) or miR combo. The day after transfection media was replaced and the cells incubated with either vehicle or the TLR3 pharmacological inhibitor CU-CPT-4a (10 µM) for a further 4 days. After incubation with the TLR3 pharmacological inhibitor, cells were cultured in normal growth media for a further 10 days.

FIGS. 1Bi-1Biii show RNA levels of the cardiomyocyte sarcomere components Myh6 (amyosin heavy chain) (FIG. 1Bi), Actn2 (αsarcomeric actinin) (FIG. 1Bii), and Tnni3 (cardiac troponin-I) (FIG. 1Biii) was determined by qPCR. N=4 independent experiments.

FIGS. 1Ci and 1Cii show cells provided miR combo (FIG. 1Ci) or miR combo and TLR3 antagonist (FIG. 1Cii) fixed and stained with anti-Actn2 antibodies (red). Nuclei were stained with DAPI (blue). Scale bar 50 microns.

FIG. 1Ciii shows quantification of immunostaining. Cells expressing Actn2 were counted and expressed as a percentage of the total cell population. N=6 independent experiments.

FIGS. 1D-1Eiii show neonatal cardiac fibroblasts were first transfected with either a control siRNA or a siRNA that targeted TLR3. Two days later, the cells were transfected again with either the negative control miR negmiR or miR combo. The day after transfection with miRNAs the media was replaced and the cells cultured in normal growth media for 14 days.

FIG. 1D shows quantification of TLR3 knockdown by qPCR. N=3 independent experiments.

FIGS. 1Ei-1Eiii show RNA levels of the cardiomyocyte structural proteins Myh6 (amyosin heavy chain) (FIG. 1Ei), Actn2 (αsarcomeric actinin) (FIG. 1Eii) and Tnni3 (cardiac troponin-I) (FIG. 1Eiii) was determined by qPCR. N=4 independent experiments. Data represented as Mean±SEM. *$P<0.001$, $P<0.01$, *$P<0.05$, ns: not significant. For A, B and D comparisons are made between miR combo and negmiR for each group. For C, comparison is made between control siRNA and siRNA targeting TLR3.

FIGS. 2Ai-2Biv show neither TLR3 inhibition nor TLR3 activation affects early stage cardiac reprogramming.

FIGS. 2Ai-2Aiv show neonatal cardiac fibroblasts were first transfected with either a control siRNA or a siRNA that targeted TLR3. Two days later, the cells were transfected again with either the negative control miR negmiR or miR combo. The day after transfection with miRNAs, the media was replaced and the cells cultured in normal growth media for 3 days. RNA levels of the cardiomyocyte-lineage commitment factors Gata4 (FIG. 2Ai), Hand2 (FIG. 2Aii), Tbx5 (FIG. 2Aiii), and Mef2C (FIG. 2Aiv) was determined by qPCR. N=9 independent experiments. Comparisons are made between miR combo+control siRNA and miR combo+TLR3 siRNA, ns: not significant. Data represented as Mean±SEM.

FIGS. 2Bi-2Biv show neonatal cardiac fibroblasts were transfected with negative control miR (negmiR) or miR combo. The day after transfection media was replaced and the cells incubated with vehicle or the TLR3 agonist Poly (I:C) LMW (low molecular weight Poly(I:C)) for a further 3 days. RNA levels of the cardiomyocyte-lineage commitment factors Gata4 (FIG. 2Bi), Hand2 (FIG. 2Bii), Tbx5 (FIG. 2Biii), and Mef2C (FIG. 2Biv) was determined by qPCR. N=6 independent experiments. Comparisons are made between miR combo+vehicle and miR combo+TLR3 agonist, ns: not significant. Data represented as Mean±SEM.

FIGS. 3Ai-3Diii show NFκB is important for miR combo reprogramming.

FIGS. 3Ai-3Biii show neonatal cardiac fibroblasts were transfected with negative control miR (negmiR) or miR combo. The day after transfection media was replaced and the cells incubated with vehicle or the NFκB antagonist Bay 11-7085. After one day of treatment, the media was replaced with normal growth media and cells cultured for a further 12 days.

FIGS. 3Ai-3Aiii RNA levels of the cardiomyocyte structural proteins Myh6 (αmyosin heavy chain) (FIG. 3Ai), Actn2 (αsarcomeric actinin) (FIG. 3Aii), and Tnni3 (cardiac troponin-I) (FIG. 3Aiii) following treatment with the NFκB antagonist Bay 11-7085 was determined by qPCR. N=3 independent experiments.

FIGS. 3Bi-3Bii shows cells provided miR combo (FIG. 3Bi) or miR combo and NFκB inhibitor (FIG. 3Bii) were fixed and stained with anti-Actn2 antibodies (red). Nuclei were stained with DAPI (blue). Scale bar 100 microns. Inset pictures are at 5× magnification.

FIGS. 3Biii shows quantification of immunostaining. Cells expressing Actn2 were counted and expressed as a percentage of the total cell population. N=3 independent experiments.

FIGS. 3C-3Diii show neonatal cardiac fibroblasts were transfected with microRNAs (negmiR or miR combo) and siRNA (control siRNA or a siRNA that targeted Ikbkb). The day after transfection with miRNAs the media was replaced and the cells cultured in normal growth media for either 4 days (to assess knockdown efficiency) or 14 days (to assess RNA levels of cardiomyocyte structural proteins).

FIG. 3C show quantification of Ikbkb knockdown by qPCR. N=3 independent experiments.

FIGS. 3Di-3Diii show RNA levels of the cardiomyocyte structural proteins Myh6 (αmyosin heavy chain) (FIG. 3Di), Actn2 (αsarcomeric actinin) (FIG. 3Dii), and Tnni3 (cardiac troponin-I) (FIG. 3Diii) was determined by qPCR. N=3 independent experiments.

Figure 6A:
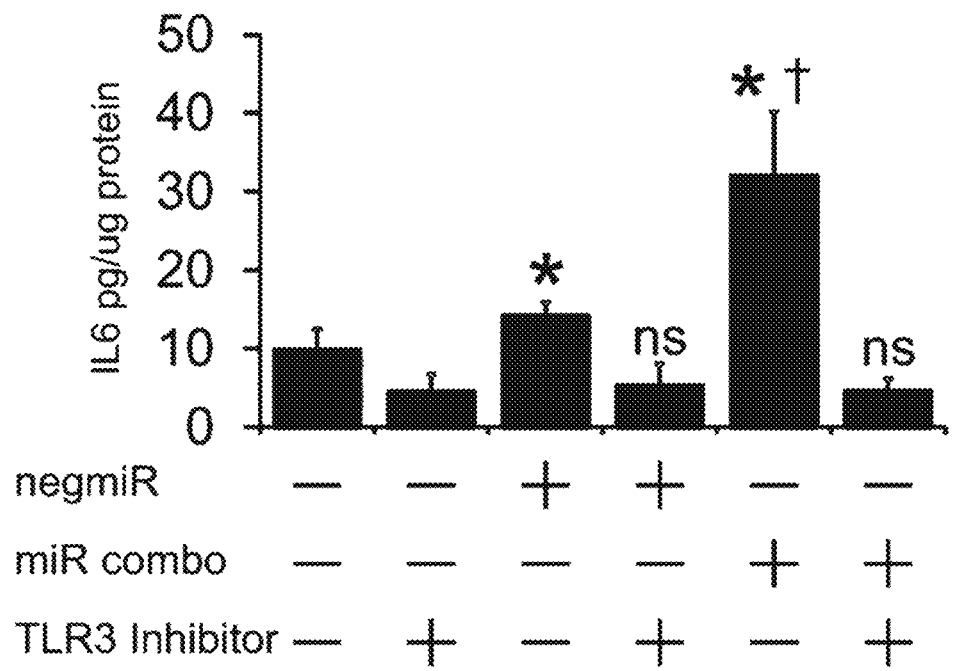

Data represented as Mean±SEM. Comparisons are made between miR combo and negmiR for each group, **P<0.01, *P<0.05, ns: not significant.

FIGS. 4A-4Dii show RelA mediates the effects of NFκB. Neonatal cardiac fibroblasts were first transfected with either a control siRNA or a siRNA that targeted the NFκB subunit RelA. Two days later, the cells were transfected again with either the negative control miR negmiR or miR combo. The day after transfection with miRNAs, the media was replaced and the cells cultured in normal growth media for 13 days.

FIG. 4A shows quantification of RelA knockdown by qPCR.

FIGS. 4Bi-4Bii show cells provided miR combo and control siRNA (FIG. 4Bi) and miR combo+RelA siRNA (FIG. 4Bii) fixed and stained with anti-Actn2 antibodies (red). Nuclei were stained with DAPI (blue). Scale bar 100 microns. Inset pictures are at 5× magnification.

FIG. 4Biii shows quantification of immunostaining. Cells expressing Actn2 were counted and expressed as a percentage of the total cell population. N=3 independent experiments.

FIGS. 4Ci-4Ciii show RNA levels of the cardiomyocyte structural proteins Myh6 (αmyosin heavy chain) (FIG. 4Ci), Actn2 (αsarcomeric actinin) (FIG. 4Cii), and Tnni3 (cardiac troponin-I) (FIG. 4Ciii) was determined by qPCR. N=3 independent experiments.

FIGS. 4Di-4Dii show RNA levels of the endodermal marker Gata6 (FIG. 4Di) and the general marker of differentiation Tgfb2 (FIG. 4Dii) were determined by qPCR. N=3 independent experiments.

Data represented as Mean±SEM. Comparisons are made between miR combo and negative control miR (negmiR) for each group, **P<0.01, *P<0.05, ns: not significant.

FIGS. 5Ai-5Bviii show the NFκB subunit RelA binds to the promoters of cardiomyocyte maturation genes.

FIGS. 5Ai-5Aviii show neonatal cardiac fibroblasts were transfected with negmiR or miR combo. After 7 days, chromatin DNA was subjected to ChIP analysis. Primers were designed to target the first 1 Kb of the indicated cardiomyocyte sarcomere genes Actn2 (FIG. 5Ai), Myh6 (FIG. 5Aii), Mypn (FIG. 5Aiii), Tnni3 (FIG. 5Aiv), Ttn (FIG. 5Av), Myoz2 (FIG. 5Avi), Tnnc1 (FIG. 5Avii), and Tnnt2 (FIG. 5Aviii), (represented by −01 Kb). Results are presented as the fold enrichment in RelA binding where percent input of the negmiR control was taken to be 1. N=3 independent experiments. Data represented as Mean±SEM. Comparisons are made between miR combo and negative control miR (negmiR), **P<0.01, *P<0.05, ns: not significant.

FIGS. 5Bi-5Bviii show neonatal cardiac fibroblasts were transfected with miR combo and either a control siRNA or a siRNA that targeted RelA. After 7 days, chromatin DNA was subjected to ChIP analysis. Primers were designed to target the first 1 Kb of the indicated cardiomyocyte sarcomere genes Actn2 (FIG. 5Bi), Myh6 (FIG. 5Bii), Mypn (FIG. 5Biii), Tnni3 (FIG. 5Biv), Ttn (FIG. 5Bv), Myoz2 (FIG. 5Bvi), Tnnc1 (FIG. 5Bvii), and Tnnt2 (FIG. 5Bviii), (represented by −01 Kb). Results are presented as the percentage of chromatin input. N=3 independent experiments. Data represented as Mean±SEM.

Figure 6B:
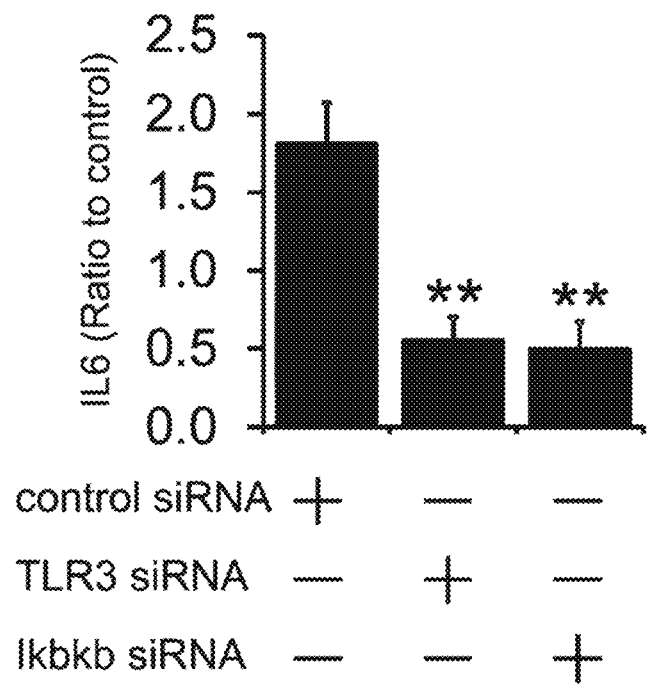

FIGS. 6A-6B show microRNAs activate TLR3.

FIG. 6A shows neonatal cardiac fibroblasts were transfected with negmiR or miR combo. A mock transfection where lipid reagent alone was added to the cells was also used. The TLR3 inhibitor CU-CPT-4a, which interferes with RNA binding to TLR3, was added one day post-transfection. IL6 concentration in the media was assessed 4 days post-transfection and values expressed as pg IL6 per μg of total protein. N=4 independent experiments. Data represented as Mean±SEM. Comparisons are made to the respective mock transfected group (*P<0.05, ns: not significant) and between negmiR and miR combo (†P<0.05).

FIG. 6B shows neonatal cardiac fibroblasts were transfected with microRNAs (mock, miR combo) and siRNA (non-targeting control, TLR3, Ikbkb). IL6 concentration in the media was assessed 4 days post-transfection and values expressed as a ratio between miR combo and mock transfected cells. N=3 independent experiments. Data represented as Mean±SEM. Comparisons are made to miR combo plus non-targeting control siRNA group, **P<0.01, *P<0.05.

FIGS. 7Ai-7Dii show TLR3 agonists enhance maturation of miR combo reprogrammed cardiomyocytes. Neonatal cardiac fibroblasts were transfected with negative control miR (negmiR) or miR combo. The day after transfection media was replaced and the cells incubated with vehicle or the TLR3 agonist Poly(I:C) LMW (low molecular weight Poly(I:C)) for a further 4 days. After incubation with the TLR3 agonist, cells were cultured in normal growth media for a further 10 days.

FIGS. 7Ai-7Aiii show RNA levels of the cardiomyocyte structural proteins Myh6 (amyosin heavy chain) (FIG. 7Ai), Actn2 (αsarcomeric actinin) (FIG. 7Aii), and Tnni3 (cardiac troponin-I) (FIG. 7Aiii) was determined by qPCR. N=5-14.

FIGS. 7Bi-7Bvi show cells provided miR combo (FIG. 7Bi, FIGS. 7Bii, and 7Biii) and miR combo and TLR3 agonist (FIG. 7Biv, FIGS. 7Bv, and 7Bvi) fixed and stained with anti-Actn2 antibodies (red). Nuclei were stained with DAPI (blue). N=6 independent experiments. Scale bar 50 microns. Inset pictures are at 5× magnification to show sarcomere structure.

FIG. 7C show quantification of immunostaining. Cells expressing Actn2 were counted and expressed as a percentage of the total cell population.

FIGS. 7Di-7Dii show neonatal cardiac fibroblasts were transfected with negative control miR (negmiR) or miR combo. The day after transfection media was replaced and the cells incubated with differentiation media (DMEM+2% FBS+ITS+AA) and the TLR3 agonist Poly(I:C) LMW for the indicated times (FIG. 7Di). Fourteen days after the transfection, the numbers of beating colonies were counted. N=4 independent experiments (FIG. 7Dii). Data represented as Mean±SEM. *Comparisons made between vehicle and TLR3 agonist for each group *P<0.001, P<0.01, *P<0.05. †Comparisons made between miR combo and negmiR for each group †††P<0.001, ††P<0.01, †P<0.05.

FIGS. 8A-8D show ICR2-activated cardiomyocyte maturation evaluated via qPCR by measuring the expression of Actn2 (FIG. 8A), Myh6 (FIG. 8B), Tnni3 (FIG. 8C), and Cacna1c (FIG. 8D).

Figure 9A:
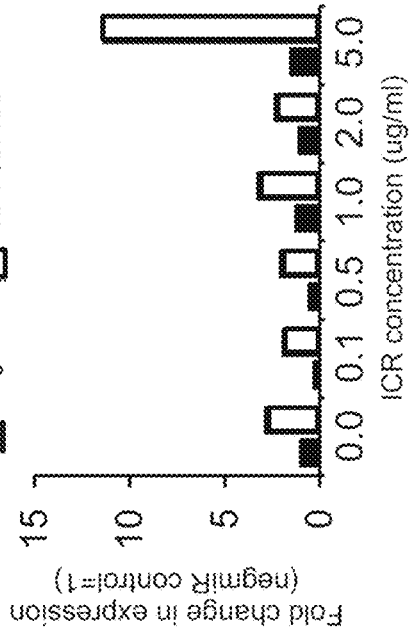
Figure 9B:
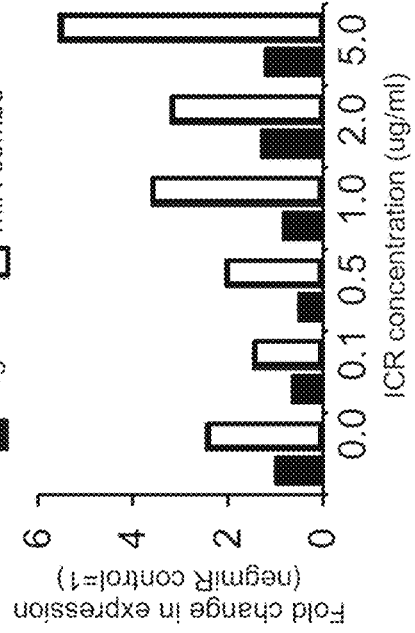
Figure 9C:
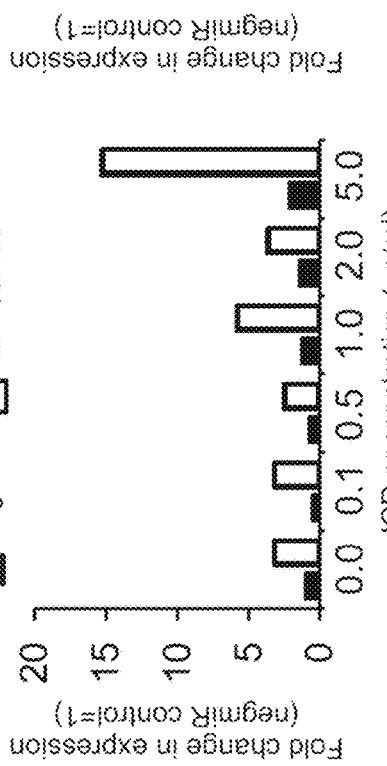
Figure 9D:
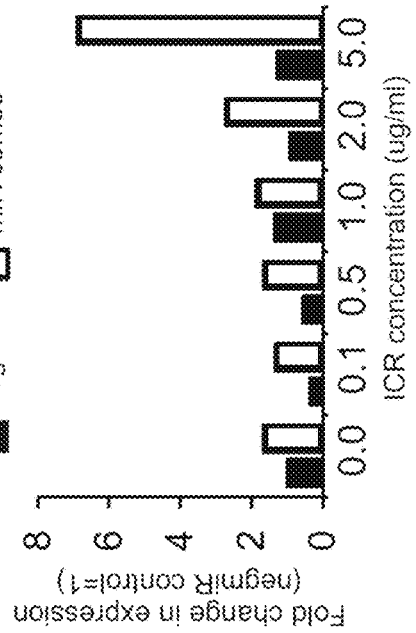

FIGS. 9A-9D shows ICR4-activated cardiomyocyte maturation evaluated via qPCR by measuring the expression of Actn2 (FIG. 9A), Myh6 (FIG. 9B), Tnni3 (FIG. 9C), and Cacna1c (FIG. 9D).

Figure 10:
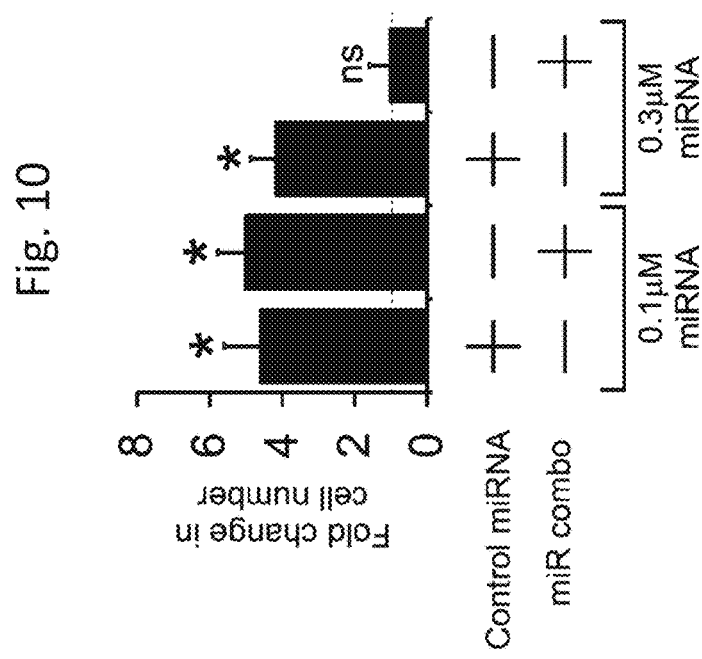

FIG. 10 shows high doses of miR combo impair normal cellular functions by measuring the change in cell number.

Figure 11A:
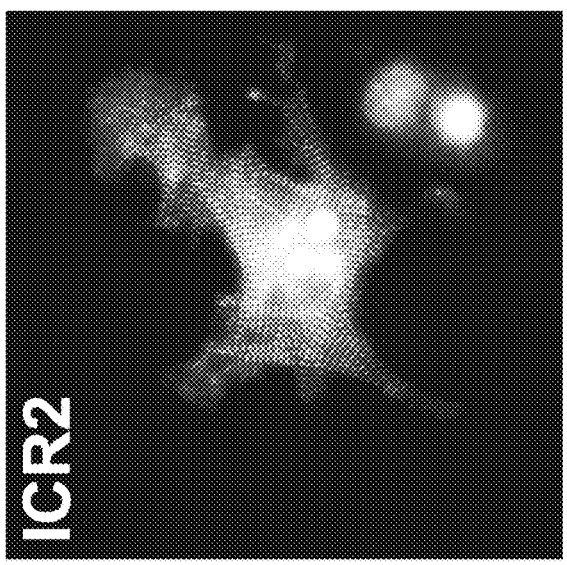
Figure 11B:
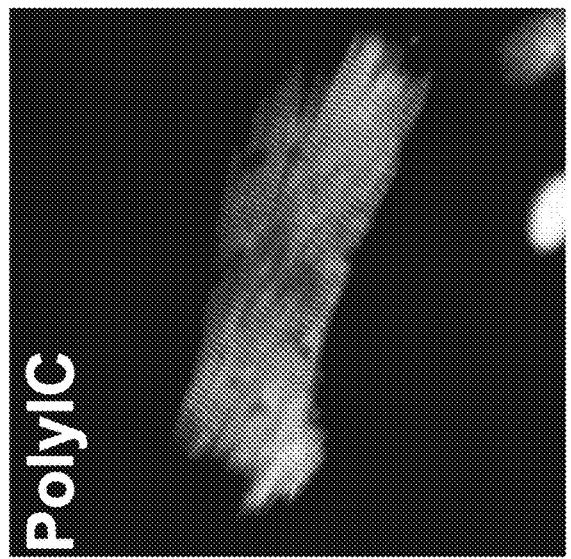

FIGS. 11A-11B show miR combo mediated maturation with ICR2 (FIG. 11A) and PolyIC (FIG. 11B) evaluated by antibody staining for a-sarcomeric actinin.

DETAILED DESCRIPTION OF THE INVENTION

Cardiomyocyte maturation may be enhanced or upregulated by agonists of the innate immune system, such as pattern recognition receptor agonists, or inhibited or downregulated by antagonists. As demonstrated in the Examples, cardiomyocyte maturation may be effectively controlled in committed cellular precursors to accelerate or retard maturation via pattern recognition receptors and associated signaling pathways.

"Pattern recognition receptors" or "PRRs" are protein receptors that detect molecules typical of pathogens and/or cellular damage. These proteins are expressed primarily by cells of the innate immune system, such as dendritic cells, macrophages, monocytes, neutrophils and epithelial cells. PRRs are used to identify pathogen-associated molecular patterns (PAMPs), which are associated with microbial pathogens, and damage-associated molecular patterns (DAMPs), which are associated with components of host's cells that are released during cell damage or death. PRRs mediate the immune response to PAMPs and DAMPs and release inflammatory cytokines.

"Pathogen-associated molecular patterns" or "PAMPs" activate immune responses by identifying exogenous molecules. Exemplary PAMPs include, without limitation, nucleic acids, bacterial lipopolysaccharides, endotoxins, bacterial flagellin, lipoteichoic acid, peptidoglycan, and unmethylated CpG motifs. Induction of the immune response to one or more exogenous molecules assists with the prevention or recovery from infection. "Damage-associated molecular patterns" or "DAMPs" activate immune responses by identifying host molecules. Exemplary DAMPs include, without limitation, nuclear or cytosolic proteins released outside the cell and nucleic acids.

Toll-like receptors are a subset of PRRs. "Toll-like receptors" or "TLRs" are a class of extracellular, membrane-bound PPRs that share a common structural motif of a leucine-rich repeat. TLRs interacting with PAMPs or DAMPs trigger signaling through NFκB resulting in the increase of inflammatory cytokines. The TLRs include TLR1, TLR2, TLR3, TLR4, TLR5, TLR6, TLR7, TLR8, TLR9, TLR10, TLR11, TLR12, and TLR13. "Cytokines" include broad category of proteins, typically between about 5 to about 20 kDa, that are involved with cell signaling, such as chemokines, interferons, interleukins, lymphokines, and tumour necrosis factors.

"NFκB" or "nuclear factor kappa-light-chain-enhancer of activated B cells" is a protein complex that controls transcription of DNA, cytokine production, and cell survival. NFκB is important in regulating cellular responses because it belongs to the category of "rapid-acting" primary transcription factors, i.e., transcription factors that are present in cells in an inactive state and do not require new protein synthesis in order to become activated. Proteins of the NFκB family share a Rel homology domain in their N-terminus. A subfamily of NF-κB proteins, including RelA, RelB, and c-Rel, have a transactivation domain in their C-termini. In contrast, the NF-κB1 and NF-κB2 proteins are synthesized as large precursors, p105, and p100, which undergo processing to generate the mature NF-κB subunits, p50 and p52, respectively.

NFκB may be activated by PAMPs and DAMPs as well as other heterologous compounds, including heterologous nucleic acids. An "activator" is a substance that increases the activity of an enzyme. An "activator of NFκB" is a substance that increase the activity of NFκB. Activators of NFκB may interact with cells to increase the activity of NFκB through various mechanisms, including, but limited to interaction with various PPRs such as TLRs or, more specifically, TLR3. "TLR3" or "Toll-like receptor 3" is a transmembrane protein encoded by the TLR3 gene that is a member of the toll-like receptor family of PRRs of the innate immune system. TLR3 recognizes nucleic acids, such as dsRNA associated with viral infections, and induces the activation of NFκB. As demonstrated in the Examples that follow, NFκB activation or inhibition may be effectively used to accelerate or retard cardiomyocyte maturation.

Enhancement or Upregulation of Cardiomyocyte Maturation.

A first aspect of the invention is compositions and methods for enhancing or upregulating cardiomyocyte maturation via the direct reprogramming of precursor cells. Reprogramming compositions for enhancing or upregulating cardiomyocyte maturation comprise (i) one or more miRs comprising a nucleotide sequence having at least 80% sequence identity to miR-1, miR-126, miR-133, miR-133a, mir-206, miR-208, miR-499, mir-4995p, and combinations thereof and (ii) an activator of NFκB. The activator of NFκB may be a TLR-pathway agonist, suitably a TLR3-pathway agonist. A "TLR-pathway agonist" is a composition or substance capable of interacting a TLR receptor or a substance associated with a TLR pathway that induces a biological response. A "TLR3-pathway agonist" is a TLR-pathway agonist that is capable of interacting with TLR3 or a substance associated with a TLR3 pathway that induces a biological response.

A "miR", also known as "miRNA" or "microRNA", is a small non-coding RNA typically comprising RNA having between about 15 to about 25 nucleotides. Some miRs are capable of folding back onto themselves to resemble dsRNA. miR-1, miR-126, miR-133, miR-133a, mir-206, miR-208, miR-499, mir-499-5p may be capable activating NFκB. Although miR-1, miR-126, miR-133, miR-133a, mir-206, miR-208, miR-499, mir-499-5p, or combinations thereof may be suitable for use activating NFκB, as used herein "activator of NFκB" excludes miR-1, miR-126, miR-133, miR-133a, mir-206, miR-208, miR-499, mir-499-5p, or any combination thereof. The use of miRs for direct reprogramming of cells to cardiomyoctes and cardiomyocytic tissue is described in US Patent Pub. No. 2014/0011281, published Jan. 9, 2014, and US Patent Pub. No. 2018/0042969, the contents of which are incorporated herein by reference in its entirety.

Nucleotide sequences of these preferred oligonucleotide constructs or combinations of constructs (and their corresponding mature forms) are listed below. Exemplary oligomeric compounds (stem-loop precursors) range in size from 50-90 nucleotides in length (or any length within that range, with an average length of approximately 70 nucleotides), and exemplary mature oligonucleotide compounds are 17 to 25 subunits in length, e.g., oligomeric compounds are 17, 18, 19, 20, 21, 22, 23, 24 or 25 subunits in length. For example, a stem-loop precursor is approximately 70 nucleotides and the mature nucleotide product is approximately 22 nucleotides in length. The uncapitalized "mir-" refers to the pre-miRNA, while a capitalized "miR-" refers to the mature form. A pre-microRNA comprises a stem-loop secondary structure.

TABLE 1 miRs

Mmu-miR-1
STEM-LOOP (SEQ ID NO: 1)
GCUUGGGACACAUACUUCUUUAUAUGCCCAUAUGAACCUGCUAAGCUAUG
GAAUGUAAAGAAGUAUGUAUUUCAGGC

TABLE 1-continued miRs

MATURE (SEQ ID NO: 2)
UGGAAUGUAAAGAAGUAUGUAU

Mmu-miR-133a
STEM-LOOP (SEQ ID NO: 3)
GCUAAAGCUGGUAAAAUGGAACCAAAUCGCCUCUUCAAUGGAUUUGGUCC
CCUUCAACCAGCUGUAGC

MATURE (SEQ ID NO: 4)
UUUGGUCCCCUUCAACCAGCUG

Mmu-miR-206
STEM-LOOP (SEQ ID NO: 5)
CCAGGCCACAUGCUUCUUUAUAUCCUCAUAGAUAUCUCAGCACUAUGGAA
UGUAAGGAAGUGUGUGGUUUUGG

MATURE (SEQ ID NO: 6)
UGGAAUGUAAGGAAGUGUGUGG

Mmu-miR-208a
STEM-LOOP (SEQ ID NO: 7)
UUCCUUUGACGGGUGAGCUUUUGGCCCGGGUUAUACCUGACACUCACGUA
UAAGACGAGCAAAAAGCUUGUUGGUCAGAGGAG

MATURE (SEQ ID NO: 8)
AUAAGACGAGCAAAAAGCUUGU

Human miR-1-1
STEM-LOOP (SEQ ID NO: 9)
UGGGAAACAUACUUCUUUAUAUGCCCAUAUGGACCUGCUAAGCUAUGGAA
UGUAAAGAAGUAUGUAUCUCA Human miR-1-2
STEM-LOOP (SEQ ID NO: 10)
ACCUACUCAGAGUACAUACUUCUUUAUGUACCCAUAUGAACAUACAAUGC
UAUGGAAUGUAAAGAAGUAUGUAUUUUUGGUAGGC MATURE SEQUENCE FOR BOTH miR1 STEM-LOOPS: (SEQ ID NO: 11)
UGGAAUGUAAAGAAGUAUGUAU Human miR-133a
Human miR-133a-1
STEM-LOOP (SEQ ID NO: 12)
ACAAUGCUUUGCUAGAGCUGGUAAAAUGGAACCAAAUCGCCUCUUCAAUG
GAUUUGGUCCCCUUCAACCAGCUGUAGCUAUGCAUUGA Human miR-133a-2
STEM-LOOP (SEQ ID NO: 13)
GGGAGCCAAAUGCUUUGCUAGAGCUGGUAAAAUGGAACCAAAUCGACUGU
CCAAUGGAUUUGGUCCCCUUCAACCAGCUGUAGCUGUGCAUUGAUGGCGC
CG MATURE SEQUENCE FOR BOTH miR133a STEM LOOPS
(SEQ ID NO: 14)
UUUGGUCCCCUUCAACCAGCUG Human miR-206
STEM-LOOP (SEQ ID NO: 15)
UGCUUCCCGAGGCCACAUGCUUCUUUAUAUCCCCAUAUGGAUUACUUUGC
UAUGGAAUGUAAGGAAGUGUGUGGUUUCGGCAAGUG MATURE SEQUENCE FOR miR-206 (SEQ ID NO: 16)
UGGAAUGUAAGGAAGUGUGUGG Human miR-208a
STEM-LOOP (SEQ ID NO: 17)
UGACGGGCGAGCUUUUGGCCCGGGUUAUACCUGAUGCUCACGUAUAAGAC
GAGCAAAAAGCUUGUUGGUCA MATURE SEQUENCE FOR miR-208 (SEQ ID NO: 18)
AUAAGACGAGCAAAAAGCUUGU Human miR-138-1
STEM-LOOP (SEQ ID NO: 19)
CCCUGGCAUGGUGUGGUGGGGCAGCUGGUGUUGUGAAUCAGGCCGUUGCC
AAUCAGAGAACGGCUACUUCACAACACCAGGGCCACACCACACUACAGG TABLE 1-continued miRs Human miR-138-2
STEM-LOOP (SEQ ID NO: 20)
CGUUGCUGCAGCUGGUGUUGUGAAUCAGGCCGACGAGCAGCGCAUCCUCU
UACCCGGCUAUUUCACGACACCAGGGUUGCAUCA MATURE SEQUENCE FOR BOTH miR-138-1 and miR-138-2
(SEQ ID NO: 21)
AGCUGGUGUUGUGAAUCAGGCCG Human miR-499-5p
STEM-LOOP (MMu-miR-499) (SEQ ID NO: 22)
GGGUGGGCAGCUGUUAAGACUUGCAGUGAUGUUUAGCUCCUCUGCAUGUG
AACAUCACAGCAAGUCUGUGCUGCUGCCU MATURE (Mmu-miR-499/Hsa-miR-499-5p; sequence is
conserved) (SEQ ID NO: 23)
UUAAGACUUGCAGUGAUGUUU Human miR-126
STEM-LOOP (Hsa-miR-126) (SEQ ID NO: 42)
CGCUGGCGACGGGACAUUAUUACUUUUGGUACGCGCUGUGACACUUCAAA
CUCGUACCGUGAGUAAUAAUGCGCCGUCCACGGCA MATURE SEQUENCE FOR miR-126 (SEQ ID NO: 43)
UCGUACCGUGAGUAAUAAUGCG Mature Sequence for miR-126-5p (SEQ ID NO: 44)
CAUUAUUACUUUUGGUACGCG As demonstrated in the Examples that follow, high doses of miRs may impair normal cellular function. As a result, it was surprisingly found that miRs in combination with a distinct activator of NFκB may enhance or upregulate cardiomyocyte maturation without the deleterious effects of high doses of miRs. Suitably, the one or more miRs contacting cells are present in an amount less than about 0.30 mM, suitably less than or equal to about 0.28 mM, 0.26 mM, 0.24 nM, 0.22 mM, 0.20 mM, 1.8 mM, 1.6 mM, 0.14 mM, 0.12 mM, or 0.10 mM.

The one or more miRs may be suitably selected from a variety of miRs, including one or more nucleotide sequences having at least 80% sequence identity to miR-1, miR126, miR-133, miR-133a, mir206, miR-208, miR-499, and mir-499-5p. Suitably the one or more MiRs may comprise a nucleotide sequence having at least 85%, 90%, 95% or more sequence identity to miR-1, miR126, miR-133, miR-133a, mir206, miR-208, miR-499, and mir-499-5p. Suitably a combination more than one miR may include any two, any three, or any four miRs having a nucleotide sequences having at least 80%, 85%, 90%, 95% or more sequence identity to miR-1, miR126, miR-133, miR-133a, mir206, miR-208, miR-499, and mir-499-5p. Suitably the combination may include four miRs having at least 80%, 85%, 90%, 95% or more sequence identity to miR-1, miR-133a, miR208, and mir-499-5p. Suitably, the combination may include four miRs consisting essentially of miR-1, miR-133a, miR208, and mir-499-5p.

Suitably the one or more miRs comprise mirl; mirl, mir133a, and mir208; mirl, mir133a, and mir206; mirl, mir133a, mir208, and mir499-Sp; mirl, mir133a, mir206, and mir499-Sp; mirl and mir133; mirl and mir138; mirl and mir206; mirl and mir208; mir133 and mir138; mir133 and mir206; mir133 and mir208; mir138 and mir206; mir138 and mir208; mir206 and mir208; mirl, mir138, and mir208; mirl, mir206, and mir208; mir138, mir206, and mir208; mirl, mir133, and mir206; mirl, mir133, and mir208; mirl, mir138, and mir206; mir133, mir138, and mir208; and mir133, mir138, and mir206. In certain embodiments, the one or more miRs consist essentially of mirl; mirl, mir133a, and mir208; mirl, mir133a, and mir206; mirl, mir133a, mir208, and mir499-Sp; mirl, mir133a, mir206, and mir499-Sp; mirl and mir133; mirl and mir138; mirl and mir206; mirl and mir208; mir133 and mir138; mir133 and mir206; mir133 and mir208; mir138 and mir206; mir138 and mir208; mir206 and mir208; mirl, mir138, and mir208; mirl, mir206, and mir208; mir138, mir206, and mir208; mirl, mir133, and mir206; mirl, mir133, and mir208; mirl, mir138, and mir206; mir133, mir138, and mir208; and mir133, mir138, and mir206.

In the Examples that follow, "miR combo" is a combination of mirl, mir133a, mir208, and mir499-5p while "negmiR" is a miRNA that does not target TLR3 and used as a negative control.

Suitably, the composition comprises an activator of NFκB such as a TLR agonist or TLR3 agonist. The TLR3 agonist may comprise an RNA composition such as a 5'-triphospate, 2'-fluoro modified non-linear RNA. The 5'-triphospate, 2'-fluoro modified non-linear RNA comprises 2'-fluoro modified pyrimidines or 2'-fluoro modified purines. The 2'-fluoro modification may be present on at least one pyrimidine or purine, and may be present on any number of pyrimidines or purines, including all of the pyrimidines, all of the purines, or all of the pyrimidines and purines. Suitably the 2'-fluoro-modification is present in 10%, 20%, 30%, 40%, 50%, 60%, 70%, 80%, 90% or 100% of the pyrimidines and/or purines or any range therebetween. The 2-fluoro modification may be present on a uridine, a cytidine, a guanine, an adenine, or any combination thereof. In some embodiments, only uridines are 2'-fluoro modified. In an embodiment, all of the uridines in the RNA are 2'-fluoro-modified, all of the cytidines in the RNA are 2'-fluoro-modified, all of the guanines in the RNA are 2'-fluoro-modified, all of the adenines in the RNA are 2'-fluoro-modified, or any combination thereof. 5'-triphospate, 2'-fluoro modified non-linear RNA is described in International Pub. No. 2018/187328, published Oct. 11, 2013, the contents of which are incorporated herein by reference in its entirety. The RNA compositions may comprise phosphorothioate modified nucleotides where a sulfur atom is substituted for a non-bridging oxygen of the phosphate. Suitably the phosphorothioate modification is present in 10%, 20%, 30%, 40%, 50%, 60%, 70%, 80%, 90% or 100% of the nucleotides or any range therebetween. In certain embodiments, the last 3 to 5 nucleotides at the 5'- and/or 3'-end of the oligonucleotide are phosphorothioate modified. In other embodiments, all of the nucleotides of the oligonucleotide are phosphorothioate modified.

The RNA compositions may comprise a blunt-end stem loop, a stem-loop having a 5'-overhang, a stem-loop having a 3'-overhang, or both a 5'-overhang and a 3'-overhang. Blunt-end stem loops comprise a 5'-terminal nucleotide and its 3'-terminal complement that are capable of hybridizing with each other, forming the stem-loop. Stem-loops having only a 5'-overhang comprise a 3'-terminal nucleotide capable of hybridizing with its complement to form the stem loop. Stem-loops having only a 3'-overhang comprise a 5'-terminal nucleotide capable of hybridizing with its complement to form the stem loop. For stem-loops having both a 5'-overhang and a 3'-overhang, neither the 5'-terminal nucleotide nor the 3'-terminal nucleotide form a part of the stem-loop.

A 5'- or 3'-overhang may be any length that allows for the RNA composition to inhibit cell growth or induce cell death. Suitably, the 5'- and/or 3'-overhang may be about 1 to about 50 nucleotides in length. In some embodiments, the 5'- and/or 3'-overhang is about 1 to about 10 nucleotides in length, including lengths of 1, 2, 3, 4, 5, 6, 7, 8, 9, or 10 nucleotides or any range of lengths therebetween. In other cases, the 5'- and/or 3'-overhang is about 10 to about 50 nucleotides in length, including lengths of 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 nucleotides or any range of lengths therebetween.

In certain embodiments, the RNA composition comprises multiple stem-loops. RNA compositions having multiple stem-loops minimally comprise a first stem-loop, a second stem-loop, and a spacer between the stem-loops.

The RNA composition may comprise a nucleotide sequence allowing for a terminal nucleotide to hybridize with it complement to form either the first stem-loop, the second stem-loop, or both. In some embodiments, the RNA composition comprises a 5'-triphosphate modified terminal nucleotide capable of hybridizing with its complementary nucleotide to form either the first or second stem-loop. In some embodiments, the RNA composition comprises a 3'-terminal nucleotide capable of hybridizing with its complementary nucleotide to form either stem-loop.

The RNA composition may comprise a 5'- or 3'-overhang associated with either or both of the first stem-loop and the second stem-loop. The 5'- or 3'-overhang associated with either the first stem-loop or the second stem-loop may be any length that allows for the RNA composition to inhibit cell growth or induce cell death. Suitably, the 5'- and/or 3'-overhang may be about 1 to about 50 nucleotides in length. In some embodiments, the 5'- and/or 3'-overhang is about 1 to about 10 nucleotides in length, including lengths of 1, 2, 3, 4, 5, 6, 7, 8, 9, of 10 nucleotides or any range of lengths therebetween. In other cases, the 5'- and/or 3'-overhang is about 10 to about 50 nucleotides in length, including lengths of 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 nucleotides or any range of lengths therebetween.

The spacer connects the stem loops in a multi-stem loop composition. In some embodiments, the spacer comprises a segment of ssRNA, a segment of dsRNA, or a combination thereof. A dsRNA segment may comprise a completely or partially hybridized segment of a segment of a first nucleotide sequence with a second nucleotide sequence. Spacers having only partial hybridization may have any number of nucleotide-pair mismatches that prevent nucleotide pairing between complementary nucleotides along the spacer. Preferably, the spacer remains thermodynamically or kinetically stable under physiological conditions. In some cases, the stem-loop has 1, 2, 3, 4, 5, or more nucleotide-pair mismatches.

The spacer may be any suitable length to provide the benefit of cytotoxicity without substantially inducing IFN production. Suitably, the length of the spacer may include between about 5 to about 100 nucleotides along a ssRNA segment, about 5 to about 100 hybridized or mismatched nucleotide pairs along a dsRNA segment, or a combination thereof. In some embodiments, the length of the spacer is about 5 to about 50 nucleotides, including lengths of 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 nucleotides or any range of lengths therebetween.

In some embodiments, the spacer is not associated with secondary structure. In other embodiments, the spacer is associated with secondary structure. Structured spacers may comprise a stem-loop, resulting in RNA compositions comprising at least a third stem-loop. The third stem-loops may be formed from the complete or partial hybridization of nucleotides and result in a hair-pin structural motif. The stem-loop may be formed from any suitable number of nucleotide pairings, including any number of nucleotide pairings between about 5 and about 30 or about 8 to about 25. In certain embodiments, the stem-loop comprises 5, 6, 7, 8, 9, 10, 11, 12, 13, 14, 15, 16, 17, 18, 19, 20, 21, 22, 23, 24, 25, 26, 27, 28, 29, or 30 nucleotide pairings or any number of nucleotide pairings therebetween. Stem-loops having only partial hybridization may have any number of nucleotide-pair mismatches that prevent nucleotide pairing between complementary nucleotides along the stem so long as the stem-loop remains stable under physiological conditions. In some cases, the stem-loop has 1, 2, 3, 4, or 5 nucleotide-pair mismatches or any range of nucleotide-pair mismatches therebetween.

Exemplary RNA oligonucleotides are provided in Table 2. The RNA compositions, referred to as Immunogenic Cancer cell-killing RNAs (ICRs), comprising 2'F pyrimidine-incorporated 5'ppp RNAs were designed and generated to contain 5'ppp and various predicted secondary structures including 3'-overhanged hairpin (ICR1, ICR1A, ICR1B, ICR1C), blunt-ended hairpin (ICR2-3, ICR2, ICR2A, ICR2B), 5' overhanged hairpin (ICR3, ICR3A, ICR3B, ICR3C), ssRNA comprising multiple stem-loops (ICR4, ICR4A) and dsRNA comprising multiple stem-loops (ICR5, which is formed from the hybridization of ICR5X and ICR5Y) at various lengths. Linear 5'ppp ssRNA (ICR-L) and long dsRNA (pIC) were also generated for comparison. As will be apparent to those of skill in the art, each of ICR1, ICR1A, ICR1B, ICR1C, ICR2A, ICR2B, ICR3, ICR3A, ICR3B, ICR3C, ICR4, ICR4A, ICR5X, and ICR5Y comprise the oligonucleotide sequence of ICR2.

TABLE 2

Single-stranded RNA

| RNA | Sequence (5'→3') | SEQ ID NO |
|---|---|---|
| ICR1 | ggaug cggua ccuga cagca uccua | SEQ ID NO: 45 |
| ICR1A | ggaug cggua ccuga cagca uccua aagug | SEQ ID NO: 24 |
| ICR1B | ggaug cggua ccuga cagca uccua aagug gugga aguga g | SEQ ID NO: 25 |
| ICR1C | ggaug cggua ccuga cagca uccua aagug gugga aguga gugag ugaaa uaaaa a | SEQ ID NO: 26 |
| ICR2-3 | ggacg uaccu gacgu cc | SEQ ID NO: 27 |

TABLE 2-continued

Single-stranded RNA

| RNA | Sequence (5'→3') | SEQ ID NO |
|---|---|---|
| ICR2-2 | ggauc guacc ugacg aucc | SEQ ID NO: 28 |
| ICR2-1 | ggauc gguac cugac agauc c | SEQ ID NO: 29 |
| ICR2 | ggaug cggua ccuga cagca ucc | SEQ ID NO: 30 |
| ICR2A | ggacg augcg guacc ugaca gcauc gucc | SEQ ID NO: 31 |
| ICR2B | ggaug cggua ccuga cagca uccac cuggg augcu gucag guacc gcauc c | SEQ ID NO: 32 |
| ICR3 | ggagc ggaug cggua ccuga cagca ucc | SEQ ID NO: 33 |
| ICR3A | gggga ggaca gcgga ugcgg uaccu gacag caucc | SEQ ID NO: 34 |
| ICR3B | ggaau gaggg gagga cagcg gauge gguac cugac agcau cc | SEQ ID NO: 35 |
| ICR3C | gggua aguga augag gggag gacag cggau gcggu accug acagc aucc | SEQ ID NO: 36 |
| ICR4 | ggaug cggua ccuga cagca uccua aacuc auggu ccaug uuugu ccaug gacca | SEQ ID NO: 37 |
| ICR4A | ggaug cggua ccuga cagca uccua aacuc auggu ccaug uuugu ccaug gacca acuac cgaca uugua ugugu ugaua uaaug u | SEQ ID NO: 38 |
| ICR5X | ggaug cggua ccuga cagca uccug aguuu aguug uugu | SEQ ID NO: 39 |
| ICR5Y | ggaug cggua ccuga cagca uccac aacaa cuaaa cuca | SEQ ID NO: 40 |
| ICR-L | gguuu uuuuu uuuuu uuuuu uuu | SEQ ID NO: 41 |

In some embodiments, the RNA composition comprises an oligonucleotide capable of forming a stem-loop. In some embodiments, the RNA composition comprises one or more stem-loops formed from the complete or partial hybridization of an oligonucleotide having at least 50% sequence identity to ICR2. In particular embodiments, the RNA composition comprises one or more stem-loops formed from the complete or partial hybridization of an oligonucleotide having at least 60%, 70%, 80%, 81%, 82%, 83%, 84%, 85%, 86%, 87%, 88%, 89%, 90%, 91%, 92,%, 93%, 94%, 95%, 96%, 97%, 98%, 99%, or 100% sequence identity to ICR2. The RNA composition may also consist essentially of one or more stem-loops formed from the complete or partial hybridization of an oligonucleotide having at least 50%, 60%, 70%, 80%, 81%, 82%, 83%, 84%, 85%, 86%, 87%, 88%, 89%, 90%, 91%, 92,%, 93%, 94%, 95%, 96%, 97%, 98%, 99%, or 100% sequence identity to ICR2.

In some embodiments, the RNA composition comprises one or more oligonucleotides having at least 50% sequence identity to ICR1, ICR1A, ICR1B, ICR1C, ICR2A, ICR2B, ICR3, ICR3A, ICR3B, ICR3C, ICR4, ICR4A, ICR5X, or ICR5Y. In particular embodiments, the RNA composition comprises one or more oligonucleotides having at least 60%, 70%, 80%, 81%, 82%, 83%, 84%, 85%, 86%, 87%, 88%, 89%, 90%, 91%, 92,%, 93%, 94%, 95%, 96%, 97%, 98%, 99%, or 100% sequence identity to any ICR1, ICR1A, ICR1B, ICR1C, ICR2A, ICR2B, ICR3, ICR3A, ICR3B, ICR3C, ICR4, ICR4A, ICR5X, or ICR5Y. The RNA composition may also consist essentially of one or more oligonucleotides having at least 50%, 60%, 70%, 80%, 81%, 82%, 83%, 84%, 85%, 86%, 87%, 88%, 89%, 90%, 91%, 92, %, 93%, 94%, 95%, 96%, 97%, 98%, 99%, or 100% sequence identity to any of ICR1, ICR1A, ICR1B, ICR1C, ICR2A, ICR2B, ICR3, ICR3A, ICR3B, ICR3C, ICR4, ICR4A, ICR5X, or ICR5Y.

In some embodiments, the activator of NFκB may be a substance other than an RNA product. Suitably, the activator of NFκB may be a microbe (e.g., a bacteria or a virus), a microbial product (e.g., a bacterial product or a viral product), an cytokine, a oxidative stressor, a physical stressor, a therapeutically used drug, a modified protein, an overexpressed protein, an overexpressed ligand, a apoptic mediator, a mitogen, a growth factor, a hormone, a physiological mediator, a chemical agent. Exemplary activators of NFκB are described in Pahl, H. L., Oncogene (1999) 18, 6853-6866, which is incorporated herein by reference in its entirety.

The TLR-pathway agonist may further comprise reprogramming media. Reprogramming media comprises a base tissue culture media, insulin-transferrin-selenium (ITS) or ascorbic acid in a somatic cell-reprogramming, e.g., fibroblast-to-cardiomyocyte-reprogramming, amount. The media may further comprise bovine serum albumin (BSA) or L-glutamine. A somatic cell reprogramming amount of insulin-transferrin-selenium is characterized by insulin being present in an amount of 10 nanomolar to 10 micromolar (e.g., 100 nM), transferrin being present in an amount of 0.002 to 1 gram per liter (e.g., 0.055 g/l), and selenium being present in an amount of 1-100 µg per liter (e.g., 6.7 µg per liter). Optionally, the media comprises 0.2 mM to 20 mM L-glutamine (e.g., 2 mM). The media may also optionally include 50 µM to 50 millimolar ascorbic acid such as 100-500 µM, e.g, 250 µM, of ascorbic acid. The use of reprogramming media for direct reprogramming of cells to cardiomyoctes and cardiomyocytic tissue is described in US Patent Pub. No. 2018/0042969, the contents of which are incorporated herein by reference in its entirety.

The reprogramming composition may comprise one or more reprogramming efficiency-enhancing molecules.

"Reprogramming efficiency-enhancing molecules" are molecules suitable for increasing the efficiency of conversion to cardiac myocytes. Exemplary reprogramming efficiency-enhancing molecules include valproic acid, bone morphogenetic protein 4 (BMP4), Janus protein tyrosine kinase (JAK) inhibitor 1, RG108, R(+) Bay K 8644, PS48, and A83-01. These agents are delivered (e.g., infused or injected) to the subject before, after, or together with the TLR-pathway agonist.

The reprogramming composition may comprise a cytoplasmic delivery agent. A "cytoplasmic delivery agent" is an agent that transport of molecules, suitably nucleic acids, across membranes. Exemplary cytoplasmic delivery agents include, without limitation, transfection agents such as DharmaFECT, liposomes, synthetic polymers, cell-penetrating peptides, nanoparticles, viral particles, electroporation buffers, nucleofection reagents, or any combination thereof.

Methods of enhancing or upregulating cardiomyocyte maturation comprise contacting a cell with an effective amount of any of the compositions described for a sufficient time such that the cell is reprogrammed into a cardiomyocyte. Suitably the cell is a fibroblast, e.g., a cardiofibroblast or a dermal fibroblast, and/or comprises cardiac fibrotic tissue.

Methods of enhancing or upregulating cardiomyocyte maturation in a subject comprising administering an effective amount of any of the compositions described or any of the pharmaceutical compositions described. Suitably the subject is in need of enhancing or upregulating cardiomyocyte maturation to alleviate symptoms, eliminate the causation of resultant symptoms either on a temporary or permanent basis, and/or to prevent or slow the appearance or to reverse the progression or severity of resultant symptoms of cardiac fibrotic tissue. Suitably the cell is a fibroblast, e.g., a cardiofibroblast or a dermal fibroblast, and/or comprises cardiac fibrotic tissue.

Inhibition or Downregulation of Cardiomyocyte Maturation

Another aspect of the invention is compositions and methods for inhibiting or downregulating cardiomyocyte maturation. Compositions for inhibiting or downregulating cardiomyocyte maturation comprise a TLR inhibitor, a NFκB inhibitor, a ikbkb inhibitor, or any combination thereof.

A "TLR inhibitor" is a composition or substance capable of interacting specifically with a TLR receptor that blocks or dampens a biological response. The TLR inhibitor may be a TLR3 inhibit. Suitably a TLR inhibitor may be a TLR antagonist. A "TLR-pathway antagonist" is a composition or substance capable of interacting a TLR receptor or a substance associated with a TLR pathway that blocks or dampens a biological response. A "TLR3-pathway antagonist" is a TLR-pathway antagonist that is capable of interacting with TLR3 or a substance associated with a TLR3 pathway that blocks or dampens a biological response. Exemplary TLR or TLR3 inhibitors include, without limitation, CU-CPT-4a, or a siRNA that interferes with the translation of the TLR protein.

A "NFκB inhibitor" is a composition or substance capable of interacting specifically with NFκB that blocks or dampens a biological response. Exemplary NFκB inhibitors include, without limitation, Bay 11-7085, or a siRNA that interferes with the translation of a NFκB protein such as RelA.

A "ikbkb inhibitor" or "inhibitor of NFκB kinase subunit beta" is a composition or substance capable of interacting specifically with ikbkb that blocks or dampens a biological response or a siRNA that interferes with the translation of the ikbkb protein.

Suitably the TLR inhibitor is a TLR3 inhibitor. e.g., an antibody, shRNA small molecule or other competitive inhibitor capable of blocking TLR3 activation and/or signaling. Suitably, the TLR inhibitor is a TLR3 inhibitor such as CU-CPT-4a used in the Examples.

Suitably the composition may further comprise a cytoplasmic delivery agent, cellular media, or any combination thereof.

Methods of inhibiting or downregulating cardiomyocyte maturation comprise contacting a cell with an effective amount of any of the compositions described for a sufficient time such that cardiomyocyte maturation is inhibited or down-regulated in the cell. Suitably the cell is a fibroblast, e.g., a cardiofibroblast or a dermal fibroblast, and/or comprises cardiac fibrotic tissue.

Pharmaceutical Compositions

The compositions utilized in the methods disclosed herein may be formulated as pharmaceutical compositions that include: (a) a therapeutically effective amount of one or more compounds as disclosed herein; and (b) one or more pharmaceutically acceptable carriers, excipients, or diluents. The pharmaceutical composition may include one or more compounds as disclosed herein in a range of about 0.1 to 2000 mg, including about 0.5 to 500 mg or about 1 to 100 mg. The pharmaceutical composition may be administered to provide the compound at a daily dose of about 0.1 to 100 mg/kg body weight, including about 0.5 to 20 mg/kg body weight or about 0.1 to 10 mg/kg body weight. In some embodiments, after the pharmaceutical composition is administered to a patient (e.g., after about 1, 2, 3, 4, 5, or 6 hours post-administration). The concentration of the compound at the site of action is an effective amount of a composition if at least some of the cells at the site of action have or will mature into a cardiomyocyte.

The compounds utilized in the methods disclosed herein may be formulated as a pharmaceutical composition that includes a carrier. For example, the carrier may be selected from the group consisting of proteins, carbohydrates, sugar, talc, magnesium stearate, cellulose, calcium carbonate, and starch-gelatin paste.

The compounds utilized in the methods disclosed herein may be formulated as a pharmaceutical composition that includes one or more binding agents, filling agents, lubricating agents, suspending agents, sweeteners, flavoring agents, preservatives, buffers, wetting agents, disintegrants, and effervescent agents.

Suitable diluents may include pharmaceutically acceptable inert fillers, such as microcrystalline cellulose, lactose, dibasic calcium phosphate, saccharides, and mixtures of any of the foregoing.

The compounds utilized in the methods disclosed herein may be formulated as a pharmaceutical composition for delivery via any suitable route. For example, the pharmaceutical composition may be administered via oral, intravenous, intramuscular, subcutaneous, topical, and pulmonary route.

The compounds utilized in the methods disclosed herein may be administered in conventional dosage forms prepared by combining the active ingredient with standard pharmaceutical carriers or diluents according to conventional procedures well known in the art.

Pharmaceutical compositions comprising the compounds may be adapted for administration by any appropriate route, for example by the oral (including buccal or sublingual), rectal, nasal, topical (including buccal, sublingual or transdermal), vaginal or parenteral (including subcutaneous, intramuscular, intravenous or intradermal) route. Such formulations may be prepared by any method known in the art of pharmacy, for example by bringing into association the active ingredient with the carrier(s) or excipient(s).

Pharmaceutical compositions adapted for oral administration may be presented as discrete units such as capsules or tablets; powders or granules; solutions or suspensions in aqueous or non-aqueous liquids; edible foams or whips; or oil-in-water liquid emulsions or water-in-oil liquid emulsions.

Pharmaceutical compositions adapted for transdermal administration may be presented as discrete patches intended to remain in intimate contact with the epidermis of the recipient for a prolonged period of time. For example, the active ingredient may be delivered from the patch by iontophoresis.

Pharmaceutical compositions adapted for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets.

The compositions and methods disclosed herein may be administered as pharmaceutical compositions and, therefore, pharmaceutical compositions incorporating the compounds are considered to be embodiments of the compositions disclosed herein. Such compositions may take any physical form which is pharmaceutically acceptable; illustratively, they can be orally administered pharmaceutical compositions. Such pharmaceutical compositions contain an effective amount of a disclosed compound, which effective amount is related to the daily dose of the compound to be administered. Each dosage unit may contain the daily dose of a given compound or each dosage unit may contain a fraction of the daily dose, such as one-half or one-third of the dose. The amount of each compound to be contained in each dosage unit can depend, in part, on the identity of the particular compound chosen for the therapy and other factors, such as the indication for which it is given. The pharmaceutical compositions disclosed herein may be formulated so as to provide quick, sustained, or delayed release of the active ingredient after administration to the patient by employing well known procedures.

The compounds for use according to the methods of disclosed herein may be administered as a single composition or a combination of compounds. For example, a composition for cardiomyocyte maturation may be administered as a single compound or in combination with another compound for cardiomyocyte maturation or that has a different pharmacological activity.

As indicated above, pharmaceutically acceptable salts of the compounds are contemplated and also may be utilized in the disclosed methods. The term "pharmaceutically acceptable salt" as used herein, refers to salts of the compounds which are substantially non-toxic to living organisms. Typical pharmaceutically acceptable salts include those salts prepared by reaction of the compounds as disclosed herein with a pharmaceutically acceptable mineral or organic acid or an organic or inorganic base. Such salts are known as acid addition and base addition salts. It will be appreciated by the skilled reader that most or all of the compounds as disclosed herein are capable of forming salts and that the salt forms of pharmaceuticals are commonly used, often because they are more readily crystallized and purified than are the free acids or bases.

Acids commonly employed to form acid addition salts may include inorganic acids such as hydrochloric acid, hydrobromic acid, hydroiodic acid, sulfuric acid, phosphoric acid, and the like, and organic acids such as p-toluenesulfonic, methanesulfonic acid, oxalic acid, p-bromophenylsulfonic acid, carbonic acid, succinic acid, citric acid, benzoic acid, acetic acid, and the like. Examples of suitable pharmaceutically acceptable salts may include the sulfate, pyrosulfate, bisulfate, sulfite, bisulfate, phosphate, monohydrogenphosphate, dihydrogenphosphate, metaphosphate, pyrophosphate, bromide, iodide, acetate, propionate, decanoate, caprylate, acrylate, formate, hydrochloride, dihydrochloride, isobutyrate, caproate, heptanoate, propiolate, oxalate, malonate, succinate, suberate, sebacate, fumarate, maleat-, butyne-1,4-dioate, hexyne-1,6-dioate, benzoate, chlorobenzoate, methylbenzoate, hydroxybenzoate, methoxybenzoate, phthalate, xylenesulfonate, phenylacetate, phenylpropionate, phenylbutyrate, citrate, lactate, alpha-hydroxybutyrate, glycolate, tartrate, methanesulfonate, propanesulfonate, naphthalene-1-sulfonate, naphthalene-2-sulfonate, mandelate, and the like.

Base addition salts include those derived from inorganic bases, such as ammonium or alkali or alkaline earth metal hydroxides, carbonates, bicarbonates, and the like. Bases useful in preparing such salts include sodium hydroxide, potassium hydroxide, ammonium hydroxide, potassium carbonate, sodium carbonate, sodium bicarbonate, potassium bicarbonate, calcium hydroxide, calcium carbonate, and the like.

The particular counter-ion forming a part of any salt of a compound disclosed herein is may not be critical to the activity of the compound, so long as the salt as a whole is pharmacologically acceptable and as long as the counterion does not contribute undesired qualities to the salt as a whole. Undesired qualities may include undesirably solubility or toxicity.

Pharmaceutically acceptable esters and amides of the compounds can also be employed in the compositions and methods disclosed herein. Examples of suitable esters include alkyl, aryl, and aralkyl esters, such as methyl esters, ethyl esters, propyl esters, dodecyl esters, benzyl esters, and the like. Examples of suitable amides include unsubstituted amides, monosubstituted amides, and disubstituted amides, such as methyl amide, dimethyl amide, methyl ethyl amide, and the like.

In addition, the methods disclosed herein may be practiced using solvate forms of the compounds or salts, esters, and/or amides, thereof. Solvate forms may include ethanol solvates, hydrates, and the like.

Subjects

As used herein, a "subject" may be interchangeable with "patient" or "individual" and means an animal, which may be a human or non-human animal, in need of treatment. A "subject in need of treatment" may include a subject having a disease, disorder, or condition that is responsive to therapy with the compositions disclosed herein. For example, a "subject in need of treatment" may include a subject having a cardiovascular disease, such as an atherosclerotic disease, or having suffered a myocardial infarction.

Methods of Treatment

As used herein, the terms "treating" or "to treat" each mean to alleviate symptoms, eliminate the causation of resultant symptoms either on a temporary or permanent basis, and/or to prevent or slow the appearance or to reverse the progression or severity of resultant symptoms of the named disease or disorder. As such, the methods disclosed herein encompass both therapeutic and prophylactic administration.

As used herein the term "effective amount" refers to the amount or dose of the compound, upon single or multiple dose administration to the subject, which provides the desired effect in the subject under diagnosis or treatment. The disclosed methods may include administering an effective amount of the disclosed compositions (e.g., as present in a pharmaceutical composition) for inducing cardiomyocyte maturation or inhibiting cardiomyocyte maturation.

An effective amount can be readily determined by the attending diagnostician, as one skilled in the art, by the use of known techniques and by observing results obtained under analogous circumstances. In determining the effective amount or dose of compound administered, a number of factors can be considered by the attending diagnostician, such as: the species of the subject; its size, age, and general health; the degree of involvement or the severity of the disease or disorder involved; the response of the individual subject; the particular compound administered; the mode of administration; the bioavailability characteristics of the preparation administered; the dose regimen selected; the use of concomitant medication; and other relevant circumstances.

A typical daily dose may contain from about 0.01 mg/kg to about 100 mg/kg (such as from about 0.05 mg/kg to about 50 mg/kg and/or from about 0.1 mg/kg to about 25 mg/kg) of each compound used in the present method of treatment.

Compositions can be formulated in a unit dosage form, each dosage containing from about 1 to about 500 mg of each compound individually or in a single unit dosage form, such as from about 5 to about 300 mg, from about 10 to about 100 mg, and/or about 25 mg. The term "unit dosage form" refers to a physically discrete unit suitable as unitary dosages for a patient, each unit containing a predetermined quantity of active material calculated to produce the desired therapeutic effect, in association with a suitable pharmaceutical carrier, diluent, or excipient.

EXAMPLES

Example: Cardiomyocyte Maturation Requires TLR3 Activated NFκB

We demonstrate that TLR3 inhibition blocked cardiomyocyte maturation; precursor cells committed to the cardiomyocyte lineage failed to express maturation genes and sarcomeres did not develop. We establish that the effects of TLR3 upon cardiomyocyte maturation were dependent upon the RelA subunit of NFκB. Importantly, under conditions that promote the development of mature cardiomyocytes NFκB became significantly enriched at the promoters of cardiomyocyte maturation genes. Furthermore, activation of the TLR3-NFκB pathway enhanced cardiomyocyte maturation. This study therefore demonstrates that the TLR3-NFκB pathway is necessary for the maturation of committed precursors into mature cardiomyocytes.

Introduction

Cardiomyocytes are an essential component of the heart. Genetic manipulation can cause abnormal cardiac morphogenesis; typically leading to embryonic lethality. This embryonic lethality is difficult to diagnose prenatally and limits our understanding of the process by which precursors commit to the cardiac lineage and mature into fully functional cardiomyocytes. Due to this hurdle, many researchers have taken to replicating cardiomyocyte development in the culture dish. Various methods have been employed including reprogramming strategies [1-8] [9-14].

In vitro modelling suggests that cardiomyocyte development has two phases; Initiation and Maturation [15-18]. In the Initiation phase of cardiomyocyte development, the precursor cell initially expresses a number of so-called pioneer transcription factors. These pioneer transcription factors induce significant epigenetic remodeling; the precursor phenotype is silenced and various genes that are necessary for commitment to the cardiomyocyte lineage are activated. The pioneer transcription factors have been identified: combined expression of Gata4, Tbx5, Mef2C and Hand1 is necessary for the initial commitment to the cardiomyocyte lineage [16]. The key epigenetic mechanism in the Initiation phase of cardiomyocyte development is histone methylation. H3K4 becomes methylated [19] whereas H3K27 is de-methylated [14]. These epigenetic modifications work in concert to activate and repress numerous genes that are necessary to stabilize commitment to the cardiomyocyte lineage. Whereas the steps in the Initiation phase of cardiomyocyte development are well known, the process of cardiomyocyte maturation has not been studied in detail.

Two recent studies have shown that TLR3 is important for reprogramming fibroblasts to iPS [20] and endothelial cells [21]. Specifically, activation of TLR3 causes global changes in the expression and activity of epigenetic modifiers that favor DNA accessibility, and phenotypic fluidity. Interestingly, TLR3 plays a role in the inflammatory response and it is known that inflammation plays a major role in the cardiac response to injury [22, 23]. We show herein that cardiomyocyte maturation requires TLR3 activated NFκB. Precursor cells that had committed to the cardiomyocyte lineage were prevented from maturing into cardiomyocytes by TLR3 inhibitors or TLR3 knockdown. Further experiments demonstrate that TLR3 controlled cardiomyocyte maturation via NFκB. Pharmacological inhibition of NFκB, as well as knockdown of Ikbkb (Inhibitor of Nuclear Factor Kappa B Kinase) which activates NFκB, prevented cardiomyocyte maturation. Moreover, conditions that induce cardiomyocyte formation induced NFκB binding to the promoters of cardiomyocyte maturation genes. Moreover, we found that microRNAs activate TLR3.

Materials & Methods

Chemicals:

TLR agonists were purchased from Invivogen (Mouse TLR1-9 agonist kit, tlrl-kit1mw). The TLR3 antagonist CU-CPT-4a, NFκB antagonist Bay 11-7085 and the AP1 antagonist SR 11302 were purchased from Tocris.

Microrna Transfection:

Mouse (C57BL/6) neonatal cardiac fibroblasts were isolated from 2 day old mouse neonates according to the method outlined in Jayawardena et al [10]. Following isolation fibroblasts were cultured in growth media containing DMEM (ATCC, Catalogue number 30-2002) supplemented with 15% v/v FBS (Thermo Scientific Hyclone Fetal bovine serum, Catalogue number SH30071.03, Lot number AXK49952) and 1% v/v penicillin/streptomycin (Gibco, Catalogue number 15140-122, 100 units Penicillin, 100 ug/ml Streptomycin). Fibroblasts were passaged once the cells had reached 70-80% confluence using 0.05% w/v trypsin (Gibco, Catalogue number 25300-054). Freshly isolated fibroblasts were labelled as Passage 0. Experiments were conducted with cells at passage 2. For all experiments, cells were seeded at 5000 cells/cm$^2$ in growth media. After 24 hours, the cells were transfected with transfection reagent alone (Dharmafect-I, ThermoScientific), with transfection reagent plus non-targeting microRNAs (negmiR), or with transfection reagent plus our previously reported combination of cardiac reprogramming microRNAs[9] (miR combo, miR-1, miR-133, miR-208, miR-499).

qPCR: Total RNA was extracted using Quick-RNA Mini-Prep Kit according to the manufacturer's instructions (Zymo Research). Total RNA (50 ng-100 ng) was converted to cDNA using a high capacity cDNA reverse transcription kit (Applied Biosystems). cDNA was used in a standard qPCR reaction involving FAM conjugated gene specific primers and TaqMan Gene Expression Master Mix (Applied Biosystems). The following primers were used for qPCR: Gapdh (Mm99999915_m1), Tnni3 (Mm00437164_m1), Actn2 (Mm00473657_m1), Myh6 (Mm00440359_m1), Cacna1c (Mm00437917_m1), Mef2C (Mm01340482_m1), Tbx5 (Mm00803518_m1), Gata4 (Mm00484689_m1) and Hand2 (Mm00439247 m1).

Immunofluorescence:

Cells were fixed with 2% v/v paraformaldehyde (EMS) as described previously [24]. Fixed cells were blocked in antibody buffer (5% w/v BSA, 0.1% v/v Tween-20, in PBS) for 1 hr at room temperature. Following blocking, cells were incubated overnight at 4° C. with a-sarcomeric actinin antibody (Sigma, A7811, 1:100) in antibody buffer. After the overnight incubation, cells were washed three times in antibody buffer. Following washing, cells were incubated with Alexa-Fluor conjugated secondary antibodies (Invitrogen, Goat Anti-mouse 594 nm) at a 1:500 dilution in antibody buffer for 1 hr at room temperature. Nuclei were stained by DAPI at 1 µg/ml for 30 minutes at room temperature in antibody buffer. Following washing in PBS to remove unbound complexes, immunofluorescence was measured using a Zeiss Axiovert 200 inverted microscope.

siRNA Knockdown:

siRNA pools (four siRNAs targeting the gene) and a negative control siRNA were purchased from Dharmacon. siRNAs were made to 200A in nuclease free water, aliquoted, and stored –80° C. until use. Fibroblasts were seeded into 12 well plates at 20,000 cells per well one day prior to transfection. On the day of transfection siRNAs were diluted to 5 µM in nuclease free water. For each well, 5 µl of the working siRNA solution was diluted with 95 µl Optimem-Serum Free media. In a separate tube 5 µl of Dharmafect-I (Dharmacon) was diluted with 95 µl Optimem-Serum Free media. After 5 minute incubation the two solutions were combined. After 20 minutes complete media lacking antibiotics was added (800 µl) and the transfection complexes added to the cells.

Chip Assays:

ChIP assays were performed according the manufacturer's instructions (Cell Signaling, SimpleChIP Enzymatic Chromatin IP kit #9003). Neonatal cardiac fibroblast nuclei were digested with 0.1 ul Micrococcal nuclease per 4×10$^6$ cells (amount of Micrococcal nuclease was empirically determined according the manufacturer's instructions). Immunoprecipitation was performed with ChIP validated antibodies: (1) rabbit IgG control (Cell Signaling, #2729); (2) Histone H3 (Cell Signaling, #4620); and (3) RelA (Cell Signaling, #8242). Immunoprecipitated DNA was quantified by qPCR (ThermoFisher, Power SYBR Green PCR Master Mix, #4367659) with primers for the promoters of Myh6 (Qiagen, EpiTect ChIP qPCR Primer Assay For Mouse Myh6, NM 010856.3 (–)08 Kb #GPM1045733(–)08A and EpiTect ChIP qPCR Primer Assay For Mouse Myh6, NM 010856.3 (–)01 Kb #GPM1045733(–)01A), Actn2 (Qiagen, EpiTect ChIP qPCR Primer Assay For Mouse Actn2, NM 033268.3 (–)01 Kb, #GPM1044781(–)01A) and Tnni3 (Qiagen, EpiTect ChIP qPCR Primer Assay For Mouse Tnni3, NM 009406.3 (–)01 Kb, #GPM1052593(–)01A). PCR reactions included the positive control Histone H3 sample and the negative control rabbit IgG sample. A serial dilution of the 2% input chromatin DNA (undiluted, 1:5, 1:25, 1:125) was used to create a standard curve and determine efficiency of amplification. Percent input was calculated and negative control IgG values subtracted. Data is presented as the fold change of percent input between miR combo and negmiR treated samples.

IL6 ELISA:

IL6 ELISA kits were from R&D Systems. Fresh media (1 ml) was added to the cells one day prior to assaying for IL6. Per manufacturer's instructions 50 ul of media was assayed and the amount of IL6 in pg/ml in the culture media was determined via a standard curve. The IL6 pg/ml value was then adjusted for the total volume of the media (1 ml) and the total cellular protein in each well to correct for differences in cell number[25].

Generating Beating Reprogrammed Cardiomyocytes:

Isolated mouse (C57BL/6) neonatal cardiac fibroblasts (passage 2) were seeded into 12-well dishes at 15000 cells/cm$^2$ in growth media. Twenty-four hours later growth media was removed and the cells transfected with negmiR or miR combo as described above. One day later, the transfection complexes were removed and media was replaced with a chemically defined reprogramming media[12] that contained 1 ug/ml Poly(I:C) (LMW). For the next four days, cells received fresh chemically defined reprogramming media [12] containing 1 ug/ml Poly(I:C) (LMW) daily. After this period, the cells received chemically defined reprogramming media [12] without Poly(I:C) (LMW) for a further 10 days. Media was replaced every other day. Beating colonies were identified with a Zeiss Axiovert 200 inverted microscope.

Images:

Images were processed with CorelDraw and Zeiss software (Axiovision Rel4.8 and Zen Blue).

Statistics:

All statistical analysis was performed using GraphPad. Experiments containing two conditions a t-test was performed. ANOVA was used for experiments with three or more conditions followed by Bonferroni post-hoc tests for comparisons between individual groups. A P-value of less than 0.05 was considered significant.

Results

TLR3 Inhibition Blocks the Maturation Phase of Cardiac Reprogramming.

The mechanisms by which committed cells mature into cardiomyocytes are unclear. Two recent studies have shown that TLR3 is important for reprogramming fibroblasts to iPS [20] and endothelial cells [21]. Moreover, TLR3 induces inflammation and inflammation is known to be important in injury. Consequently, we asked ourselves if TLR3 played a hitherto unknown role in the development of mature cardiomyocytes. We were interested in TLRs as these receptors are key mediators of the inflammatory responses in the heart.

In the first instance, we tested our hypothesis with the specific TLR3 pharmacological inhibitor CU-CPT-4a [26, 27]. We were specifically interested in the maturation phase of cardiac reprogramming. To that end, we carried out an initial screen for the mRNA levels for components of that are involved in cardiomyocyte sarcomere function. We used our previously described miR combo to induce cardiac reprogramming. MiR combo is a combination of four microRNAs (miR-1, -133, -208, -499) that robustly induces cardiac reprogramming both in vitro and in vivo[9, 11-14]. As shown in FIG. 1A miR combo significantly induced the expression of 13 components of the cardiomyocyte sarcomere. The effect of miR combo upon cardiomyocyte sarcomere gene expression was completely abolished by the TLR3 pharmacological inhibitor CU-CPT-4a (FIG. 1).

We verified our initial screen by measuring the mRNA levels of three components of the cardiomyocyte sarcomere: Myh6 (αmyosin heavy chain), Actn2 (αsarcomeric actinin) and Tnni3 (cardiac troponin-I). As we observed in our initial screen, pharmacological inhibition of TLR3 completely inhibited miR combo reprogramming with respect to the expression of Myh6, Actn2, and Tnni3 (FIGS. 1Bi-1Biii). We then assessed the effects of TLR3 inhibition upon the maturation of reprogrammed fibroblasts at the cellular level. The ability of miR combo to generate mature cardiomyocytes with organized sarcomeres was completely inhibited by CU-CPT-4a (FIGS. 1Ci-1Ciii). These results were then verified by siRNA mediated knockdown of TLR3. Knockdown of TLR3 by siRNA was robust (FIG. 1D) and completely abrogated miR combo reprogramming with respect to the expression of Myh6, Actn2, and Tnni3 (FIGS. 1Ei-1Eiii).

Neither TLR3 Inhibition Nor TLR3 Activation Affects the Initiation Phase of Cardiac Reprogramming.

Following these results, we wanted to investigate the mechanism by which TLR3 influenced the maturation of reprogrammed cells in more detail. During heart development, in the initial phase of differentiation of precursors into cardiomyocytes epigenetic processes act to turn on expression of the cardiomyocyte-lineage commitment factors Gata4, Hand2, Tbx5 and Mef2C are expressed[28]. Similarly, increased expression of these cardiomyocyte-lineage commitment factors in fibroblasts represents the initial phase of cardiac reprogramming [1-6, 9, 12, 14]. We found that the expression of the cardiomyocyte-lineage commitment factors Gata4, Hand2, Tbx5 and Mef2C, that was induced by miR combo, was not affected by either TLR3 knockdown (FIGS. 2Ai-2Aiv) or by TLR3 activation (FIGS. 2Bi-2Biv). This data indicates that the effects of TLR3 upon the cardiac reprogramming were not due to changes in the initiation phase of cardiac reprogramming.

TLR3 Controls the Maturation Phase of Cardiac Reprogramming Via the RelA Subunit of NFκB.

TLR3 mediates the activation of a number of transcription factors[22]. Of these transcription factors, two mediate the vast majority of the effects of TLR3: AP1 and NFκB[22]. Consequently, we hypothesized that TLR3 would influence maturation of reprogrammed cells via AP1 and/or NFκB. Pharmacological inhibition of AP1 had no effect on the ability of miR combo to reprogram fibroblasts (data not shown). In contrast, the pharmacological inhibition of NFκB completely inhibited miR combo reprogramming at both the RNA (FIGS. 3Ai-3Aiii) and protein (FIGS. 3Bi-3Biii) level.

We further verified a role for NFκB in the maturation of reprogrammed cells by targeting Ikbkb; a kinase that is necessary for NFκB activation[29]. Knockdown of Ikbkb was robust (FIG. 3C). Importantly, knockdown of Ikbkb completely inhibited miR combo reprogramming with respect to the expression of the cardiomyocyte maturation markers Myh6, Actn2, and Tnni3 (FIGS. 3Di-3Diii). In agreement with the studies described above, Ikbkb knockdown did not influence the initiation phase of cardiac reprogramming (data not shown). Moreover, Ikbkb knockdown did not affect miR combo mediated suppression of endodermal, ectodermal and vascular markers (data not shown).

There are five NFκB proteins: NF-κB1 (p105/p50); NF-κB2 (p100/p52); RelA (p65); RelB; and c-Rel. Only RelA, RelB and c-Rel induce transcription. We focused on RelA as it is the most highly expressed Rel protein. Knockdown of RelA, which was found to be robust (FIG. 4A), prevented the appearance of Actn2(+) cells in miR combo transfected fibroblasts (FIGS. 4Bi-4Biii). Effects at the protein level were also observed at the mRNA level; targeting RelA with siRNA completely inhibited miR combo reprogramming with respect to sarcomere-related gene expression (FIGS. 4Ci-4Ciii). We also noted that RelA knockdown had no effect on the expression of the endodermal marker Gata6 or the general differentiation marker Tgfb2 (FIGS. 4Di-4Dii).

Finally, we wanted to determine how RelA controlled the expression of cardiomyocyte maturation genes. Consequently, we used ChIP assays to determine if miR combo induced RelA binding to the promoters of components of the cardiomyocyte sarcomere. Significant enrichment of RelA was observed at the Actn2, Myh6, Mypn and Tnni3 promoters (FIGS. 5Ai-5Aiv) following miR combo treatment. Similar enrichment was also observed for the Ttn, Myoz2, Tnnc1 and Tnnt2 promoters; however, this failed to reach $P<0.05$ significance (FIGS. 5Av-5Aviii). There was no enrichment in the unrelated gene RPL30 (data not shown). Targeted knockdown of RelA completely removed the ChIP signal. This result verified that RelA was indeed binding to the promoters of the cardiomyocyte sarcomere genes (FIGS. 5Bi-5Bviii).

MicroRNAs Activate TLR3

The pharmacological inhibitor and siRNA mediated knockdown experiments suggested that miR combo activated TLR3. To test this further we transfected cells with microRNAs and assessed TLR3 activity by measuring IL6 secretion into the media. IL6 secretion is an accepted measurement of the activity of TLRs, including TLR3 [30-37]. When compared to mock transfected fibroblasts both the control non-targeting miRNA (negmiR) and miR combo significantly induced IL6 secretion (FIG. 6A). Comparisons between negmiR and miR combo indicated that miR combo had the stronger effect. The induction of IL6 secretion by microRNAs was TLR3 dependent; the addition of the TLR3 inhibitor CU-CPT-4a, which inhibits interaction between RNA and TLR3, completely ablated the effect of negmiR and miR combo upon IL6 secretion (FIG. 6A). Targeted knockdown of TLR3 or Ikbkb inhibited miR combo induced IL6 secretion; further validating that miR combo activated the TLR3-NFκB pathway (FIG. 6B).

Pharmacological Activation of TLR3 Enhances Maturation of Reprogrammed Fibroblasts.

Following the identification of the mechanism by which TLR3 controlled miR combo reprogramming, we next examined if stimulation of TLR3 could enhance the efficiency of miR combo. As expected, miR combo increased RNA levels of Myh6, Actn2 and Tnni3 (FIGS. 7Ai-7Aiii). The effect of miR combo upon Myh6, Actn2 and Tnni3 expression was significantly enhanced by the addition of the TLR3 agonist Poly(I:C) (FIGS. 7Ai-7Aiii). Intriguingly, Poly(I:C) also induced expression of Myh6, Actn2 and Tnni3 in the control negmiR samples (FIGS. 7Ai-7Aiii). This effect, considering that Poly(I:C) had no effect on the expression of cardiomyocyte-commitment factors, is further evidence that the TLR3 pathway controls the maturation phase of cardiac reprogramming. We then performed immunostaining to determine if the effects at the RNA level were also observed at the protein level. Indeed, we found that the number of Actn2(+) cells that formed in response to miR combo treatment was increased by the TLR3 agonist Poly (I:C) (FIGS. 7Bi-7Bvi, with quantification provided in FIG. 7C). We also noted that TLR3 activation enhanced sarcomere maturation (see figure inserts in FIGS. 7Bi-7Bvi).

In accordance with our previous study [9], we found that transfecting fibroblasts with miR combo led to the appearance of spontaneously beating colonies (FIGS. 7Di-7Dii). The ability of miR combo to form spontaneously beating colonies was increased 3-fold by the addition of the TLR3 agonist Poly(I:C) (FIGS. 7Di-7Dii). Importantly, mature beating colonies were observed within one week of transfection.

Discussion

In this study we demonstrate that TLR3 activated NFκB is an important mechanism for the maturation of committed precursors into cardiomyocytes.

Our study clearly identified a role for TLR3 activated NFκB specifically in the maturation phase of cardiac reprogramming. This differs from previous studies which have linked TLR3 activated NKκB to the reprogramming to iPS [20] or endothelial cells [21]. These previous studies demonstrate that TLR3-NFκB causes global changes in the expression and activity of epigenetic modifiers that favors increased DNA accessibility. In this open chromatin configuration, the activation of the pluripotency program by the Yamanaka factors[20], or the induction of endothelial lineage by trans-differentiation factors[21], is facilitated. In these studies, the epigenetic plasticity that is induced by TLR3 activation is largely mediated by NFκB, as shown using pharmacological or molecular antagonists of NFκB.

We have extended this work by examining the role of TLR in maturation of cardiomyocyte precursors. We found that TLR3 activation increased the binding of NFκB directly to cardiomyocyte sarcomere genes. By contrast, we found that TLR3 played no role in the commitment of precursors into the cardiomyocyte lineage. TLR3 inhibition or knockdown did not influence the expression of various transcription factors that are necessary for commitment into the cardiomyocyte lineage.

As mentioned above, we found that miR combo induced RelA binding to the promoters of various components of the cardiomyocyte sarcomere. Canonical RelA binding sites are present in the Myh6 promoter but are absent in the promoters of the Actn2, Mypn and Tnni3 genes. Non-canonical RelA binding sites have been identified in other genes [43], and they are present in in the Actn2, Mypn and Tnni3 gene promoters. However, it is also possible that RelA influences cardiac gene expression through an indirect mechanism. RelA, and NFκB, have been shown to modulate gene expression through binding to other proteins [44-46] as well as by modulating the activity of the epigenetic machinery. It is possible that the RelA subunit of NFκB plays a similar role in cardiomyocyte maturation.

Our study suggests that microRNAs directly activate TLR3. Several TLRs are known to bind to nucleic acids: TLR3; TLR7; TLR8; and TLR9 [47]. TLR3 recognizes double-stranded (ds) RNA; whereas TLR7 and TLR8 bind to single-stranded RNA. In contrast, TLR9 is activated by unmethylated CpG sequences in DNA molecules [47]. Only a limited number of reports have demonstrated that microRNAs bind to TLRs. Even though microRNAs are dsRNA molecules, the microRNAs miR-21, miR-29a, and Let-7b bind, and activate, TLR7 and TLR8 [48, 49]. With respect to TLR3, it was originally suggested that microRNAs might be too small to induce efficient dimerization, and thus activation, of TLR3 [50]. However, this assumption is likely to need revision both in light of our results as well as the recent report that the plant derived microRNA FvmiR168 binds to dendritic cell TLR3[51]. We found that miR combo more strongly induced TLR3 than the negative control microRNA used in our studies. This may suggest that TLR3 activation by microRNAs is sequence dependent. In support of this notion, siRNA mediated activation of TLRs has been shown to be sequence dependent [52].

Example: TLR3 Activation Enhances Cardiomyocyte Maturation

Cardiac fibroblasts were transfected with miR combo or negmiR (control) and incubated with various concentrations of ICR2 (FIGS. 8A-8D) or ICR4 (FIGS. 9A-9D) for 4 days. Reprograming was evaluated via qPCR, where we measure the expression of genes that are necessary for sarcomere function (e.g. Actn2, Myh6, Tnni3) as well as cardiac ion channels (Cacna1c). Gene expression was evaluated at day 14. To further verify that ICR2 induced maturation, cardiac fibroblasts were incubated with miR combo in addition to PolyIC or ICR2 for 14 days. Sarcomeres were visualized by antibody staining for a-sarcomeric actinin (FIGS. 11A and 11B).

Example: High Doses of miR Combo Impair Normal Cellular Functions

Neonatal cardiac fibroblasts were transfected with either 0.1 mM or 0.3 mM miR combo. Equivalent concentrations of a non-targeting miRNA were used as a control. Cell number is represented as a fold change derived from GAPDH expression at day 0 and day 14 (FIG. 10). The dotted line indicates the cell number at day 0. Cell number increased significantly in both concentrations of control miR and the standard concentration of miR combo. High concentrations of miR combo impaired normal cell number growth either by inhibiting cell proliferation or by increasing rate of cell death. N=2.

REFERENCES

1. Qian L, Huang Y, Spencer C I, et al. In vivo reprogramming of murine cardiac fibroblasts into induced cardiomyocytes. Nature. 2012; 485:593-598.
2. Fu J D, Stone N R, Liu L, et al. Direct reprogramming of human fibroblasts toward a cardiomyocyte-like state. Stem Cell Reports. 2013; 1:235-247.
3. Nam Y J, Song K, Luo X, et al. Reprogramming of human fibroblasts toward a cardiac fate. Proc Natl Acad Sci USA. 2013; 110:5588-5593.
4. Song K, Nam Y J, Luo X, et al. Heart repair by reprogramming non-myocytes with cardiac transcription factors. Nature. 2012; 485:599-604.
5. Nam Y J, Lubczyk C, Bhakta M, et al. Induction of diverse cardiac cell types by reprogramming fibroblasts with cardiac transcription factors. Development 2014; 141:4267-4278.
6. Ifkovits J L, Addis R C, Epstein J A, et al. Inhibition of TGFbeta signaling increases direct conversion of fibroblasts to induced cardiomyocytes. PLoS One. 2014; 9:e89678.
7. Narita H, Shima F, Yokoyama J, et al. Engraftment and morphological development of vascularized human iPS cell-derived 3D-cardiomyocyte tissue after xenotransplantation. Sci Rep. 2017; 7:13708.
8. Yamakawa H, Ieda M. Strategies for heart regeneration: approaches ranging from induced pluripotent stem cells to direct cardiac reprogramming. Int Heart J. 2015; 56:1-5.
9. Jayawardena T M, Egemnazarov B, Finch E A, et al. MicroRNA-mediated in vitro and in vivo direct reprogramming of cardiac fibroblasts to cardiomyocytes. Circ Res. 2012; 110:1465-1473.
10. Jayawardena T, Mirotsou M, Dzau V J. Direct reprogramming of cardiac fibroblasts to cardiomyocytes using microRNAs. Methods Mol Biol. 2014; 1150:263-272.
11. Jayawardena T M, Finch E A, Zhang L, et al. MicroRNA induced cardiac reprogramming in vivo: evidence for mature cardiac myocytes and improved cardiac function. Circ Res. 2015; 116:418-424.
12. Wang X, Hodgkinson C P, Lu K, et al. Selenium Augments microRNA Directed Reprogramming of Fibroblasts to Cardiomyocytes via Nanog. Sci Rep. 2016; 6:23017.
13. Li Y, Dal-Pra S, Mirotsou M, et al. Tissue-engineered 3-dimensional (3D) microenvironment enhances the direct reprogramming of fibroblasts into cardiomyocytes by microRNAs. Sci Rep. 2016; 6:38815.
14. Dal-Pra S, Hodgkinson C P, Mirotsou M, et al. Demethylation of H3K27 Is Essential for the Induction of Direct Cardiac Reprogramming by miR Combo. Circ Res. 2017.
15. Kathiriya I S, Nora E P, Bruneau B G. Investigating the transcriptional control of cardiovascular development. Circ Res. 2015; 116:700-714.
16. Bruneau B G. Signaling and transcriptional networks in heart development and regeneration. Cold Spring Harb Perspect Biol. 2013; 5:a008292.
17. David L, Polo J M. Phases of reprogramming. Stem Cell Res. 2014; 12:754-761.
18. Buganim Y, Faddah D A, Jaenisch R. Mechanisms and models of somatic cell reprogramming. Nat Rev Genet 2013; 14:427-439.
19. Liu Z, Chen O, Zheng M, et al. Re-patterning of H3K27me3, H3K4me3 and DNA methylation during fibroblast conversion into induced cardiomyocytes. Stem Cell Res. 2016; 16:507-518.
20. Lee J, Sayed N, Hunter A, et al. Activation of innate immunity is required for efficient nuclear reprogramming. Cell. 2012; 151:547-558.
21. Sayed N, Wong W T, Ospino F, et al. Transdifferentiation of human fibroblasts to endothelial cells: role of innate immunity. Circulation. 2015; 131:300-309.
22. Hodgkinson C P, Ye S. Toll-like receptors, their ligands, and atherosclerosis. Scientific World Journal. 2011; 11:437-453.
23. Lin Y T, Verma A, Hodgkinson C P. Toll-like receptors and human disease: lessons from single nucleotide polymorphisms. Curr Genomics. 2012; 13:633-645.
24. Hodgkinson C P, Naidoo V, Patti K G, et al. Abi3 bp is a multifunctional autocrine/paracrine factor that regulates mesenchymal stem cell biology. Stem Cells. 2013; 31:1669-1682.
25. Hodgkinson C P, Laxton R C, Patel K, et al. Advanced glycation end-product of low density lipoprotein activates the toll-like 4 receptor pathway implications for diabetic atherosclerosis. Arterioscler Thromb Vasc Biol. 2008; 28:2275-2281.
26. Cheng K, Wang X, Yin H. Small-molecule inhibitors of the TLR3/dsRNA complex. J Am Chem Soc. 2011; 133: 3764-3767.
27. Faksh A, Britt R D, Jr., Vogel E R, et al. TLR3 activation increases chemokine expression in human fetal airway smooth muscle cells. Am J Physiol Lung Cell Mol Physiol. 2016; 310:L202-211.
28. Bruneau B G. Transcriptional regulation of vertebrate cardiac morphogenesis. Circ Res. 2002; 90:509-519.
29. Banerjee A, Gerondakis S. Coordinating TLR-activated signaling pathways in cells of the immune system. Immunol Cell Biol. 2007; 85:420-424.
30. Hahnlein J S, Ramwadhdoebe T H, Semmelink J F, et al. Distinctive expression of T cell guiding molecules in human autoimmune lymph node stromal cells upon TLR3 triggering. Sci Rep. 2018; 8:1736.
31. Bernard J J, Cowing-Zitron C, Nakatsuji T, et al. Ultraviolet radiation damages self noncoding RNA and is detected by TLR3. Nat Med. 2012; 18:1286-1290.
32. Schaefer T M, Fahey J V, Wright J A, et al. Innate immunity in the human female reproductive tract: antiviral response of uterine epithelial cells to the TLR3 agonist poly(I:C). J Immunol. 2005; 174:992-1002.
33. Town T, Jeng D, Alexopoulou L, et al. Microglia recognize double-stranded RNA via TLR3. J Immunol. 2006; 176:3804-3812.
34. Kumar A, Zhang J, Yu F S. Toll-like receptor 3 agonist poly(I:C)-induced antiviral response in human corneal epithelial cells. Immunology. 2006; 117:11-21.
35. Lan T, Wang D, Bhagat L, et al. Design of synthetic oligoribonucleotide-based agonists of Toll-like receptor 3 and their immune response profiles in vitro and in vivo. Org Biomol Chem. 2013; 11:1049-1058.
36. Mastri M, Shah Z, McLaughlin T, et al. Activation of Toll-like receptor 3 amplifies mesenchymal stem cell trophic factors and enhances therapeutic potency. Am J Physiol Cell Physiol. 2012; 303:C1021-1033.
37. Sironi M, Biasin M, Cagliani R, et al. A common polymorphism in TLR3 confers natural resistance to HIV-1 infection. J Immunol. 2012; 188:818-823.
38. Epelman S, Liu P P, Mann D L. Role of innate and adaptive immune mechanisms in cardiac injury and repair. Nat Rev Immunol. 2015; 15:117-129.
39. Nahrendorf M, Swirski F K. Innate immune cells in ischaemic heart disease: does myocardial infarction beget myocardial infarction? Eur Heart J. 2016; 37:868-872.
40. Kis A, Yellon D M, Baxter G F. Role of nuclear factor-kappa B activation in acute ischaemia-reperfusion injury in myocardium. Br J Pharmacol. 2003; 138:894-900.
41. Mann D L. The emerging role of innate immunity in the heart and vascular system: for whom the cell tolls. Circ Res. 2011; 108:1133-1145.
42. Newton K, Dixit V M. Signaling in innate immunity and inflammation. Cold Spring Harb Perspect Biol. 2012; 4.
43. Wong D, Teixeira A, Oikonomopoulos S, et al. Extensive characterization of NF-kappaB binding uncovers non-canonical motifs and advances the interpretation of genetic functional traits. Genome Biol. 2011; 12:R70.
44. Ashburner B P, Westerheide S D, Baldwin A S, Jr. The p65 (RelA) subunit of NF-kappaB interacts with the histone deacetylase (HDAC) corepressors HDAC1 and HDAC2 to negatively regulate gene expression. Mol Cell Biol. 2001; 21:7065-7077.
45. Yamit-Hezi A, Nir S, Wolstein O, et al. Interaction of TAFII105 with selected p65/RelA dimers is associated with activation of subset of NF-kappa B genes. J Biol Chem. 2000; 275:18180-18187.
46. Islam K N, Mendelson C R. Potential role of nuclear factor kappaB and reactive oxygen species in cAMP and cytokine regulation of surfactant protein-A gene expression in lung type II cells. Mol Endocrinol. 2002; 16:1428-1440.
47. Chen X, Liang H, Zhang J, et al. microRNAs are ligands of Toll-like receptors. RNA. 2013; 19:737-739.
48. Fabbri M, Paone A, Calore F, et al. MicroRNAs bind to Toll-like receptors to induce prometastatic inflammatory response. Proc Natl Acad Sci USA. 2012; 109:E2110-2116.
49. Lehmann S M, Kruger C, Park B, et al. An unconventional role for miRNA: let-7 activates Toll-like receptor 7 and causes neurodegeneration. Nat Neurosci. 2012; 15:827-835.
50. Wang Y, Liu L, Davies D R, et al. Dimerization of Toll-like receptor 3 (TLR3) is required for ligand binding. J Biol Chem. 2010; 285:36836-36841.
51. Cavalieri D, Rizzetto L, Tocci N, et al. Plant microRNAs as novel immunomodulatory agents. Sci Rep. 2016; 6:25761.
52. Judge A D, Sood V, Shaw J R, et al. Sequence-dependent stimulation of the mammalian innate immune response by synthetic siRNA. Nat Biotechnol. 2005; 23:457-462.
53. Matsumoto M, Tatematsu M, Nishikawa F, et al. Defined TLR3-specific adjuvant that induces NK and CTL activation without significant cytokine production in vivo. Nat Commun. 2015; 6:6280.

We claim:

1. A reprogramming composition comprising:
   (a) one or more miRs comprising a nucleotide sequence having at least 95% A sequence identity to miR-1 (SEQ ID NO: 11), miR-133a (SEQ ID NO: 14), miR-208 (SEQ ID NO: 18), and mir-499-5p (SEQ ID NO: 23), and combinations thereof; and
   (b) a TLR3 agonist.

2. The composition of claim 1, wherein the TLR3 agonist comprises a modified 5'-triphosphate, 2' fluoro modified non-linear RNA, or a poly(I:C) compound.

3. The composition of claim 2, wherein the non-linear RNA comprises an oligonucleotide having at least 80% sequence identity to ICR2 (SEQ ID NO: 30), ICR4 (SEQ ID NO: 37), ICR4A (SEQ ID NO: 38), ICR5X (SEQ ID NO: 39), or ICR5Y (SEQ ID NO: 40).

4. The composition of claim 3, wherein the non-linear RNA comprises an oligonucleotide having at least 80% sequence identity to ICR2 (SEQ ID NO: 30).

5. The composition of claim 3, wherein the non-linear RNA comprises an oligonucleotide having at least 80% sequence identity to ICR4 (SEQ ID NO: 37).

6. The composition of claim 1, further comprising a cytoplasmic delivery agent, reprogramming media, a reprogramming efficiency-enhancing molecule, or any combination thereof.

7. The composition of claim 1, wherein the one or more miRs consists essentially of: miR-1 (SEQ ID NO: 11), miR-133a (SEQ ID NO: 14), miR: 208 (SEQ ID NO: 18), and mir-499-5p (SEQ ID NO: 23).

8. The composition of claim 1, wherein the one or more miRs comprise a portion of a pre-miRNA.

9. A pharmaceutical composition comprising an effective amount of the composition of claim 1 and one or more pharmaceutically acceptable carriers, excipients, or diluents.

10. A method for enhancing or upregulating cardiomyocyte maturation in a cell comprising contacting the cell with an effective amount of the reprogramming composition of claim 1 for a sufficient time such that the cell is reprogrammed into a cardiomyocyte.

11. The method of claim 10, wherein the cell is a fibroblast.

12. The method of claim 10, wherein the cell comprises cardiac fibrotic tissue.

13. A method of enhancing or upregulating cardiomyocyte maturation in a subject comprising administering (i) an effective amount of the of the composition of claim 1 or (ii) a pharmaceutical composition comprising the effective amount of the composition of claim 1 and one or more pharmaceutically acceptable carriers, excipients, or diluents.

14. The method of claim 13, wherein the subject has a cardiovascular disease or has suffered a myocardial infarction.

15. The composition of claim 1, comprising two or more miRs selected from the group consisting of miR-1, miR-133a, miR-208, and mir-499-5p.

16. The composition of claim 1, comprising three or more miRs selected from the group consisting of miR-1, miR-133a, miR-208, and mir-499-5p.

17. The composition of claim 1, comprising miR-1, miR-133a, miR-208, and mir-499-5p.

18. A reprogramming composition comprising miR-1, miR-133a, miR-208, and mir-499-5p and an activator of NκKB.

* * * * *

UNITED STATES PATENT AND TRADEMARK OFFICE
CERTIFICATE OF CORRECTION

PATENT NO. : 11,512,290 B2  
APPLICATION NO. : 16/982964  
DATED : November 29, 2022  
INVENTOR(S) : Conrad Hodgkinson et al.

Page 1 of 1

It is certified that error appears in the above-identified patent and that said Letters Patent is hereby corrected as shown below:

In the Specification

Column 2, Line 41, "amyosin" should be --αmyosin--.

Column 2, Line 63, "amyosin" should be --αmyosin--.

Column 3, Line 40, "amyosin" should be --αmyosin--.

Column 3, Line 64, "amyosin" should be --αmyosin--.

Column 4, Line 23, "amyosin" should be --αmyosin--.

Column 5, Line 24, "amyosin" should be --αmyosin--.

Column 13, Line 11, "gauge" should be --gaugc--.

Column 26, Line 5, "FvmiR168" should be --FvMiR168--.

In the Claims

Claim 1, Column 43, Line 36, "95% A sequence" should be --95% sequence--.

Signed and Sealed this
Twenty-first Day of May, 2024

Katherine Kelly Vidal
*Director of the United States Patent and Trademark Office*